(12) United States Patent
Shah et al.

(10) Patent No.: US 7,153,867 B2
(45) Date of Patent: Dec. 26, 2006

(54) USE OF NITROGEN SUBSTITUTED THALIDOMIDE ANALOGS FOR THE TREATMENT OF MACULAR DEGENERATOR

(75) Inventors: Jamshed H. Shah, Brookeville, MD (US); Barry P. Conner, Laurel, MD (US); Glenn M. Swartz, Mt. Airy, MD (US); Kimberly A. Hunsucker, Alpharetta, GA (US); John Rougas, Germantown, MD (US); Robert J. D'Amato, Lexington, MA (US); Victor Pribluda, Silver Spring, MD (US); Anthony Treston, Rockville, MD (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 10/213,294

(22) Filed: Aug. 6, 2002

(65) Prior Publication Data

US 2003/0139451 A1     Jul. 24, 2003

Related U.S. Application Data

(60) Provisional application No. 60/310,261, filed on Aug. 6, 2001.

(51) Int. Cl.
*A61K 31/445* (2006.01)
(52) U.S. Cl. .................................................. 514/323
(58) Field of Classification Search ................ 514/323, 514/235.2, 557, 625, 417, 414
See application file for complete search history.

(56) References Cited

U.S. PATENT DOCUMENTS

| | | | | |
|---|---|---|---|---|
| 4,053,615 | A * | 10/1977 | Boyle et al. ................. 514/318 |
| 5,593,990 | A * | 1/1997 | D'Amato ................. 514/235.2 |
| 5,629,327 | A * | 5/1997 | D'Amato ................. 514/323 |
| 5,635,517 | A * | 6/1997 | Muller et al. ................. 514/323 |
| 5,712,291 | A * | 1/1998 | D'Amato ................. 514/323 |
| 5,955,476 | A * | 9/1999 | Muller et al. ................. 514/323 |
| 6,114,355 | A * | 9/2000 | D'Amato ................. 514/323 |
| 6,281,230 | B1 * | 8/2001 | Muller et al. ................. 514/323 |
| 6,306,879 | B1 * | 10/2001 | Germann et al. ................. 514/323 |
| 6,316,471 | B1 * | 11/2001 | Muller et al. ................. 514/323 |
| 6,380,239 | B1 * | 4/2002 | Muller et al. ................. 514/417 |
| 6,429,212 | B1 * | 8/2002 | Hashimoto ................. 514/309 |
| 6,458,810 | B1 * | 10/2002 | Muller et al. ................. 514/323 |
| 6,476,052 | B1 * | 11/2002 | Muller et al. ................. 514/323 |
| 6,555,554 | B1 * | 4/2003 | Muller et al. ................. 514/323 |
| 6,667,316 | B1 * | 12/2003 | Man et al. ................. 514/323 |
| 2003/0045552 | A1 * | 3/2003 | Robarge et al. ................. 514/323 |

FOREIGN PATENT DOCUMENTS

WO         92/14455      *  9/1992   ................. 514/323
WO    WO 9803502  A1  *  1/1998

OTHER PUBLICATIONS

"New Cancer Drugs No 'Magic bullet', but Promising", Reuters News, 2001.*
Strategy Aims to Starve Rather Than Poison Cancer, Daniel Haney, 1999.*
Cecil TextBook of Medicine, 20th Edition, vol. 1, 1997.*
"Angiogenesis and the Role of Epigenetics in Metastasis", Coomber et al., Clinical a& Experimental Metastasis, 20:215-227, 2003.*
"Thalidomide and Prednisolone Inhibit Growth Factor-INduced Human Retinal Pigment Epithelium Cell Proliferation in Vitro", Kaven et al., abstract, vol. 215, No. 4, 2001.*
"Age-Related Macular Degeneration", Drug Therapy, vol. 342, No. 7, pp. 483-492, 2000.*
"A Common Pharmacore for Taxol and the Epothilones Based on the Biological Activity of a Taxane Molecule Lacking a C-13 Side Chain", He et al., Biochemistry 2000, 39, pp. 3972-3978.*
"Thalidomide Analogs and PDE4 Inhibition", Muller et al., Biorganic & Medicinal Chemistry Letters, 1998, pp. 2669-2674.*
Montrucchio et al., 1994, *Tumor Necrosis Factor α-induced Angiogenesis Depends on In Situ Platelet-activating Factor Biosynthesis*, J. Exp. Med. 180:337-382.

* cited by examiner

*Primary Examiner*—Brian Kwon
(74) *Attorney, Agent, or Firm*—Jones Day

(57) ABSTRACT

The present invention comprises a group of compounds that effectively inhibit angiogenesis. More specifically, nitrogen-substituted thalidomide analogs and di-substituted thalidomide analogs have been shown to inhibit angiogenesis. Importantly, these compounds can be administered orally.

2 Claims, 14 Drawing Sheets

Scheme-1: Synthesis of 3-Hydoxylamino-Thalidomide 4
3-Hydoxylamino-Thalidomide 3
3-Nitro-Thalidomide

Synthesis of S(-)-3-amino-thalidomide

Synthesis of 3-(6-Amino-phthalimidino)-glutarimide

Synthesis of 3-(4-aminophthalimidino)-glutaric acid.HCl 3-(4-aminophthalimidino)-glutaric acid.HCl Synthesis of 4 or 6 or 7 3-(hydrazino-phthalimidino)-gluteramide

Synthesis of 3-(4-Amino-phthalimidino)-gluteramide

Synthesis of 3-(2-aminobenzoylamido)-gluteramide 3-(2-aminobenzoylamido)-gluteramide Synthesis of 3-4-Diamino-Thalidomide Synthesis of 3,6-Diamino and Dihydrazino-Thalidomide

USE OF NITROGEN SUBSTITUTED THALIDOMIDE ANALOGS FOR THE TREATMENT OF MACULAR DEGENERATOR

CROSS REFERENCE TO RELATED APPLICATION

The present application claims the priority of now abandoned U.S. Provisional Patent Application Ser. No. 60/310, 261 filed Aug. 6, 2001, which is incorporated herein by reference.

TECHNICAL FIELD

The present invention relates to methods and compositions for preventing unwanted angiogenesis in a human or animal. More particularly, the present invention relates to a method for preventing unwanted angiogenesis, particularly in angiogenesis dependent or associated diseases, by administration of compounds such as thalidomide and related compounds.

BACKGROUND OF THE INVENTION

Angiogenesis is the generation of new blood vessels into a tissue or organ. Under normal physiological conditions, humans and animals undergo angiogenesis only in very specific, restricted situations. For example, angiogenesis is normally observed in wound healing, fetal and embryonal development, and formation of the corpus luteum, endometrium and placenta.

Angiogenesis is controlled through a highly regulated system of angiogenic stimulators and inhibitors. The control of angiogenesis has been found to be altered in certain disease states and, in many cases, pathological damage associated with the diseases is related to uncontrolled angiogenesis. Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. Endothelial cells, lining the lumen of blood vessels, then protrude through the basement membrane. Angiogenic stimulants induce the endothelial cells to migrate through the eroded basement membrane. The migrating cells form a "sprout" off the parent blood vessel where the endothelial cells undergo mitosis and proliferate. The endothelial sprouts merge with each other to form capillary loops, creating a new blood vessel.

Persistent, unregulated angiogenesis occurs in many disease states, tumor metastases, and abnormal growth by endothelial cells. The diverse pathological disease states in which unregulated angiogenesis is present have been grouped together as angiogenic-dependent or angiogenic-associated diseases.

One example of a disease mediated by angiogenesis is ocular neovascular disease. This disease is characterized by invasion of new blood vessels into the structures of the eye, such as the retina or cornea. It is the most common cause of blindness and is involved in approximately twenty eye diseases. In age-related macular degeneration, the associated visual problems are caused by an ingrowth of choroidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma, and retrolental fibroplasia. Other diseases associated with corneal neovascularization include, but are not limited to, epidemic keratoconjunctivitis, Vitamin A deficiency, contact lens overwear, atopic keratitis, superior limbic keratitis, pterygium keratitis sicca, Sjögren's disease, acne rosacea, phylectenulosis, syphilis, Mycobacteria infections, lipid degeneration, chemical burns, bacterial ulcers, fungal ulcers, Herpes simplex infection, Herpes zoster infections, protozoan infections, Kaposi's sarcoma, Mooren's ulcer, Terrien's marginal degeneration, marginal keratolysis, rheumatoid arthritis, systemic lupus, polyarteritis, trauma, Wegener's syndrome, sarcoidosis, scleritis, Stevens-Johnson's disease, pemphigoid, and radial keratotomy.

Diseases associated with retinal/choroidal neovascularization include, but are not limited to, diabetic retinopathy, macular degeneration, sickle cell anemia, sarcoidosis, syphilis, pseudoxanthoma elasticum, Paget's disease, vein occlusion, artery occlusion, carotid obstructive disease, chronic uveitis/vitritis, Mycobacteria infections, lyme's disease, systemic lupus erythematosis, retinopathy of prematurity, Eales' disease, Behcet's disease, infections causing retinitis or choroiditis, presumed ocular histoplasmosis, Best's disease, myopia, optic pits, Stargardt's disease, pars planitis, chronic retinal detachment, hyperviscosity syndromes, toxoplasmosis, trauma and post-laser complications. Other eye-related diseases include, but are not limited to, diseases associated with rubeosis (neovascularization of the angle) and diseases caused by the abnormal proliferation of fibrovascular or fibrous tissue, including all forms of prolific vitreoretinopathy.

Another angiogenesis associated disease is rheumatoid arthritis. The blood vessels in the synovial lining of the joints undergo angiogenesis. In addition to forming new vascular networks, the endothelial cells release factors and reactive oxygen species that lead to pannus growth and cartilage destruction. Angiogenesis may also play a role in osteoarthritis. The activation of the chondrocytes by angiogenic-related factors contributes to the destruction of the joint. At a later stage, the angiogenic factors promote new bone growth. Therapeutic intervention that prevents the bone destruction could halt the progress of the disease and provide relief for persons suffering with arthritis.

Chronic inflammation may also involve pathological angiogenesis. Such diseases as ulcerative colitis and Crohn's disease show histological changes with the ingrowth of new blood vessels and the inflamed tissues. Bartonelosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity.

The hypothesis that tumor growth is angiogenesis-dependent was first proposed in 1971. (Folkman, *New Eng. J. Med.*, 285:1182–86 (1971)). In its simplest terms, this hypothesis states: "Once tumor 'take' has occurred, every increase in tumor cell population must be preceded by an increase in new capillaries converging on the tumor." Tumor 'take' is currently understood to indicate a prevascular phase of tumor growth in which a population of tumor cells occupying a few cubic millimeters volume, and not exceeding a few million cells, can survive on existing host microvessels. Expansion of tumor volume beyond this phase requires the induction of new capillary blood vessels. For example, pulmonary micrometastases in the early prevascular phase in mice would be undetectable except by high power microscopy on histological sections.

Examples of the indirect evidence which support this concept include:

(1) The growth rate of tumors implanted in subcutaneous transparent chambers in mice is slow and linear before neovascularization, and rapid and nearly exponential after neovascularization. (Algire, et al., *J. Nat. Cancer Inst.*, 6:73–85 (1945)).

(2) Tumors grown in isolated perfused organs where blood vessels do not proliferate are limited to 1–2 mm$^3$ but expand rapidly to >1000 times this volume when they are transplanted to mice and become neovascularized. (Folkman, et al., *Annals of Surgery*, 164:491–502 (1966)).

(3) Tumor growth in the avascular cornea proceeds slowly and at a linear rate, but switches to exponential growth after neovascularization. (Gimbrone, Jr., et al., *J. Nat. Cancer Inst.*, 52:421–27 (1974)).

(4) Tumors suspended in the aqueous fluid of the anterior chamber of the rabbit eye remain viable, avascular, and limited in size to <1 mm$^3$. Once they are implanted on the iris vascular bed, they become neovascularized and grow rapidly, reaching 16,000 times their original volume within 2 weeks. (Gimbrone, Jr., et al., *J. Exp. Med.*, 136:261–76).

(5) When tumors are implanted on the chick embryo chorioallantoic membrane, they grow slowly during an avascular phase of >72 hours, but do not exceed a mean diameter of 0.93+0.29 mm. Rapid tumor expansion occurs within 24 hours after the onset of neovascularization, and by day 7 these vascularized tumors reach a mean diameter of 8.0+2.5 mm. (Knighton, *British J. Cancer*, 35:347–56 (1977)).

(6) Vascular casts of metastases in the rabbit liver reveal heterogeneity in size of the metastases, but show a relatively uniform cut-off point for the size at which vascularization is present. Tumors are generally avascular up to 1 mm in diameter, but are neovascularized beyond that diameter. (Lien, et al., *Surgery*, 68:334–40 (1970)).

(7) In transgenic mice which develop carcinomas in the beta cells of the pancreatic islets, pre-vascular hyperplastic islets are limited in size to <1 mm. At 6–7 weeks of age, 4–10% of the islets become neovascularized, and from these islets arise large vascularized tumors of more than 1000 times the volume of the pre-vascular islets. (Folkman, et al., *Nature*, 339:58–61 (1989)).

(8) A specific antibody against VEGF (vascular endothelial growth factor) reduces microvessel density and causes "significant or dramatic" inhibition of growth of three human tumors which rely on VEGF as their sole mediator of angiogenesis (in nude mice). The antibody does not inhibit growth of the tumor cells in vitro. (Kim, et al., *Nature*, 362:841–44 (1993)).

(9) Anti-bFGF monoclonal antibody causes 70% inhibition of growth of a mouse tumor which is dependent upon secretion of bFGF as its only mediator of angiogenesis. The antibody does not inhibit growth of the tumor cells in vitro. (Hori, et al., *Cancer Res.*, 51:6180–84 (1991)).

(10) Intraperitoneal injection of bFGF enhances growth of a primary tumor and its metastases by stimulating growth of capillary endothelial cells in the tumor. The tumor cells themselves lack receptors for bFGF, and bFGF is not a mitogen for the tumors cells in vitro. (Gross, et al., *Proc. Am. Assoc. Cancer Res.*, 31:79 (1990)).

(11) A specific angiogenesis inhibitor (AGM-1470) inhibits tumor growth and metastases in vivo, but is much less active in inhibiting tumor cell proliferation in vitro. It inhibits vascular endothelial cell proliferation half-maximally at 4 logs lower concentration than it inhibits tumor cell proliferation. (Ingber, et al., *Nature*, 48:555–57 (1990)). There is also indirect clinical evidence that tumor growth is angiogenesis dependent.

(12) Human retinoblastomas that are metastatic to the vitreous develop into avascular spheroids which are restricted to less than 1 mm$^3$ despite the fact that they are viable and incorporate $^3$H-thymidine (when removed from an enucleated eye and analyzed in vitro).

(13) Carcinoma of the ovary metastasizes to the peritoneal membrane as tiny avascular white seeds (1–3 mm$^3$) These implants rarely grow larger until one or more of them becomes neovascularized.

(14) Intensity of neovascularization in breast cancer (Weidner, et al., *New Eng. J. Med.*, 324:1–8 (1991); Weidner, et al., *J Nat. Cancer Inst.*, 84:1875–87 (1992)) and in prostate cancer (Weidner, et al., *Am. J. Pathol.*, 143(2): 401–09 (1993)) correlates highly with risk of future metastasis.

(15) Metastasis from human cutaneous melanoma is rare prior to neovascularization. The onset of neovascularization leads to increased thickness of the lesion and an increased risk of metastasis. (Srivastava, et al., *Am. J. Pathol.*, 133: 419–23 (1988)).

(16) In bladder cancer, the urinary level of an angiogenic protein, bFGF, is a more sensitive indicator of status and extent of disease than is cytology. (Nguyen, et al., *J. Nat. Cancer Inst.*, 85:241–42 (1993)).

Thus, it is clear that angiogenesis plays a major role in the metastasis of cancer. If this angiogenic activity could be repressed or eliminated, then the tumor, although present, would not grow. In the disease state, prevention of angiogenesis could avert the damage caused by the invasion of the new microvascular system. Therapies directed at control of the angiogenic processes could lead to the abrogation or mitigation of these diseases.

Angiogenesis has been associated with a number of different types of cancer, including solid tumors and blood-borne tumors. Solid tumors with which angiogenesis has been associated include, but are not limited to, rhabdomyosarcomas, retinoblastoma, Ewing's sarcoma, neuroblastoma, and osteosarcoma. Angiogenesis is also associated with blood-borne tumors, such as leukemias, any of various acute or chronic neoplastic diseases of the bone marrow in which unrestrained proliferation of white blood cells occurs, usually accompanied by anemia, impaired blood clotting, and enlargement of the lymph nodes, liver and spleen. It is believed to that angiogenesis plays a role in the abnormalities in the bone marrow that give rise to leukemia-like tumors and multiple myeloma-like diseases.

One of the most frequent angiogenic diseases of childhood is the hemangioma. A hemangioma is a tumor composed of newly-formed blood vessels. In most cases the tumors are benign and regress without intervention. In more severe cases, the tumors progress to large cavernous and infiltrative forms and create clinical complications. Systemic forms of hemangiomas, hemangiomatoses, have a high mortality rate. Therapy-resistant hemangiomas exist that cannot be treated with therapeutics currently in use.

Angiogenesis is also responsible for damage found in heredity diseases such as Osler-Weber-Rendu disease, or heredity hemorrhagic telangiectasia. This is an inherited disease characterized by multiple small angiomas, tumors of blood or lymph vessels. The angiomas are found in the skin and mucous membranes, often accompanied by epitaxis (nose bleeds) or gastrointestinal bleeding and sometimes with pulmonary or hepatic arterioyenous fistula.

What is needed, therefore, is a composition and method which can inhibit angiogenesis. What is also needed is a composition and method which can inhibit the unwanted growth of blood vessels, especially in tumors.

Angiogenesis is also involved in normal physiological processes, such as reproduction and wound healing. Angiogenesis is an important step in ovulation and also in implantation of the blastula after fertilization. Prevention of angiogenesis could be used to induce amenorrhea, to block ovulation, or to prevent implantation by the blastula.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

Several compounds have been used to inhibit angiogenesis. Taylor, et al. (*Nature*, 297:307 (1982)) have used protamine to inhibit angiogenesis. The toxicity of protamine limits its practical use as a therapeutic. Folkman, et al. (*Science*, 221:719 (1983), and U.S. Pat. Nos. 5,001,116 and 4,994,443) have disclosed the use of heparin and steroids to control angiogenesis. Steroids, such as tetrahydrocortisol, which lack gluccocorticoid and mineralocorticoid activity, have been found to be angiogenic inhibitors.

Other factors found endogenously in animals, such as a 4 kDa glycoprotein from bovine vitreous humor and a cartilage derived factor, have been used to inhibit angiogenesis. Cellular factors, such as interferon, inhibit angiogenesis. For example, interferon alpha or human interferon beta have been shown to inhibit tumor-induced angiogenesis in mouse dermis stimulated by human neoplastic cells. Interferon beta is also a potent inhibitor of angiogenesis induced by allogeneic spleen cells. (Sidky, et al., *Cancer Res.*, 47:5155–61 (1987)). Human recombinant interferon (alpha/A) was reported to be successfully used in the treatment of pulmonary hemangiomatosis, an angiogenesis-induced disease. (White, et al., *New Eng. J. Med.*, 320:1197–1200 (1989)).

Other agents which have been used to inhibit angiogenesis include ascorbic acid ethers and related compounds. (Japanese Kokai Tokkyo Koho No. 58-13 (1978)). Sulfated polysaccharide DS 4152 also inhibits angiogenesis. (Japanese Kokai Tokkyo Koho No. 63-119500). Additional anti-angiogenic compounds include Angiostatin® (U.S. Pat. Nos. 5,639,725; 5,792,845; 5,885,795; 5,733,876; 5,776,704; 5,837,682; 5,861,372, and 5,854,221) and Endostatin™ (U.S. Pat. No. 5,854,205).

Another compound which has been shown to inhibit angiogenesis is thalidomide. (D'Amato, et al., *Proc. Natl. Acad. Sci.*, 90:4082–85 (1994)). Thalidomide is a hypnosedative that has been successfully used to treat a number of angiogenesis-associated diseases, such as rheumatoid arthritis (Gutierrez-Rodriguez, *Arthritis Rheum.*, 27 (10):1118–21 (1984); Gutierrez-Rodriguez, et al., *J. Rheumatol.*, 16(2): 158–63 (1989)), Behcet's disease (Handley, et al., *Br. J. Dermatol.*, 127 Suppl, 40:67–8 (1992); Gunzler, *Med. Hypotheses*, 30(2):105–9 (1989)), graft versus host rejection (Field, et al., *Nature*, 211(55): 1308–10 (1966); Heney, et al., *Br. J. Haematol.*, 78 (1):23–7 (1991)), Mycobacteria diseases (Vicente, et al., *Arch. Intern. Med.*, 153(4):534 (1993)), Herpes simplex and Herpes zoster infections (Naafs, et al., *Int. J. Dermatol.*, 24(2):131–4 (1985)), chronic inflammation, ulcerative colitis (Meza, et al., *Drug Ther*, 23 (11): 74–80, 83 (1993); Powell, et al., *Br. J. Dermatol.*, 113 Suppl 28: 141–4 (1985)), leprosy (Barnes, et al., *Infect. Immun.*, 60(4):1441–46 (1992)) and lupus (Burrows, *BMJ*, 307: 939–40 (1993)).

Although thalidomide has minimal side effects in adults, it is a potent teratogen. Thus, there are concerns regarding its use in women of child-bearing age. Although minimal, there are a number of side effects which limit the desirability of thalidomide as a treatment. One such side effect is drowsiness. In a number of therapeutic studies, the initial dosage of thalidomide had to be reduced because patients became lethargic and had difficulty functioning normally. Another side effect limiting the use of thalidomide is peripheral neuropathy, in which individuals suffer from numbness and disfunction in their extremities. Thus, improved methods and compositions are needed that are easily administered and capable of inhibiting angiogenesis.

SUMMARY OF THE INVENTION

In accordance with the present invention, compositions and methods are provided that are effective in inhibiting unwanted angiogenesis. These compositions are easily administered by different routes including oral and can be given in dosages that are safe and provide angiogenic inhibition at internal sites. The present invention provides a method of treating mammalian diseases mediated by undesired and uncontrolled angiogenesis by administering a composition comprising an anti-angiogenic compound in a dosage sufficient to inhibit angiogenesis.

The present invention is especially useful for treating certain ocular neovascular diseases such as macular degeneration. The compounds which are contemplated as part of the present invention preferably can be given orally to the patient and thereby halt the progression of the disease. Other disease that can be treated using the present invention are diabetic retinopathy, neovascular glaucoma and retrolental fibroplasia.

Analogs of thalidomide that can be used in accordance with the present invention include compounds included in the following general formulae. Examples of compounds that have anti-angiogenic properties are included within the following three formulae (A), (B) or (C):

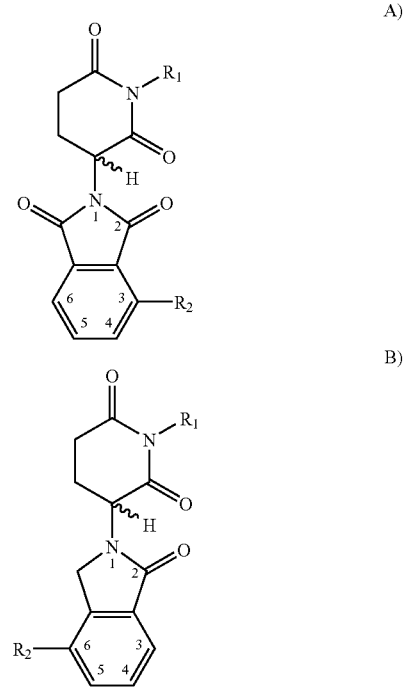

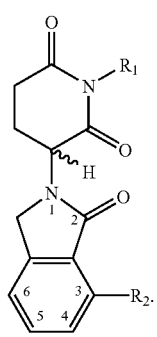

C)

In an another aspect of the present invention, includes di-substituted thalidomide analogs may be employed. Examples of di-substituted thalidomide analogs that have anti-angiogenic properties are compounds included within the following general formula D):

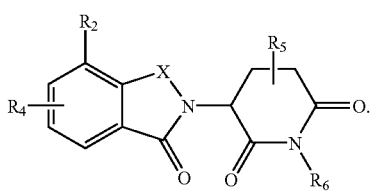

D)

Accordingly, the present invention preferably provides one or more of the following objects.

One object of the present invention is to provide a compound and method to inhibit unwanted angiogenesis in a human or animal.

It is yet another object of the present invention to provide a composition of inhibiting angiogenesis by oral administration of the composition.

It is another object of the present invention to provide a treatment for diseases mediated by angiogenesis.

It is yet another object of the present invention to provide a treatment for macular degeneration.

It is yet another object of the present invention to provide a treatment for all forms of proliferative vitreoretinopathy including those forms not associated with diabetes.

It is yet another object of the present invention to provide a treatment for solid tumors.

It is yet another object of the present invention to provide a method and composition for the treatment of blood-born tumors such as leukemia.

It is another object of the present invention to provide a method and composition for the treatment of hemangioma.

It is another object of the present invention to provide a method and composition for the treatment of retrolental fibroplasia.

It is another object of the present invention to provide a method and composition for the treatment of psoriasis.

It is another object of the present invention to provide a method and composition for the treatment of Kaposi's sarcoma.

It is another object of the present invention to provide a method and composition for the treatment of Crohn's diseases.

It is another object of the present invention to provide a method and composition for the treatment of diabetic retinopathy.

Other features and advantages of the invention will be apparent from the following description of preferred embodiments thereof.

These and other objects, features and advantages of the present invention will become apparent after a review of the following detailed description of the disclosed embodiments and the appended claims.

DETAILED DESCRIPTION

Figure 1:
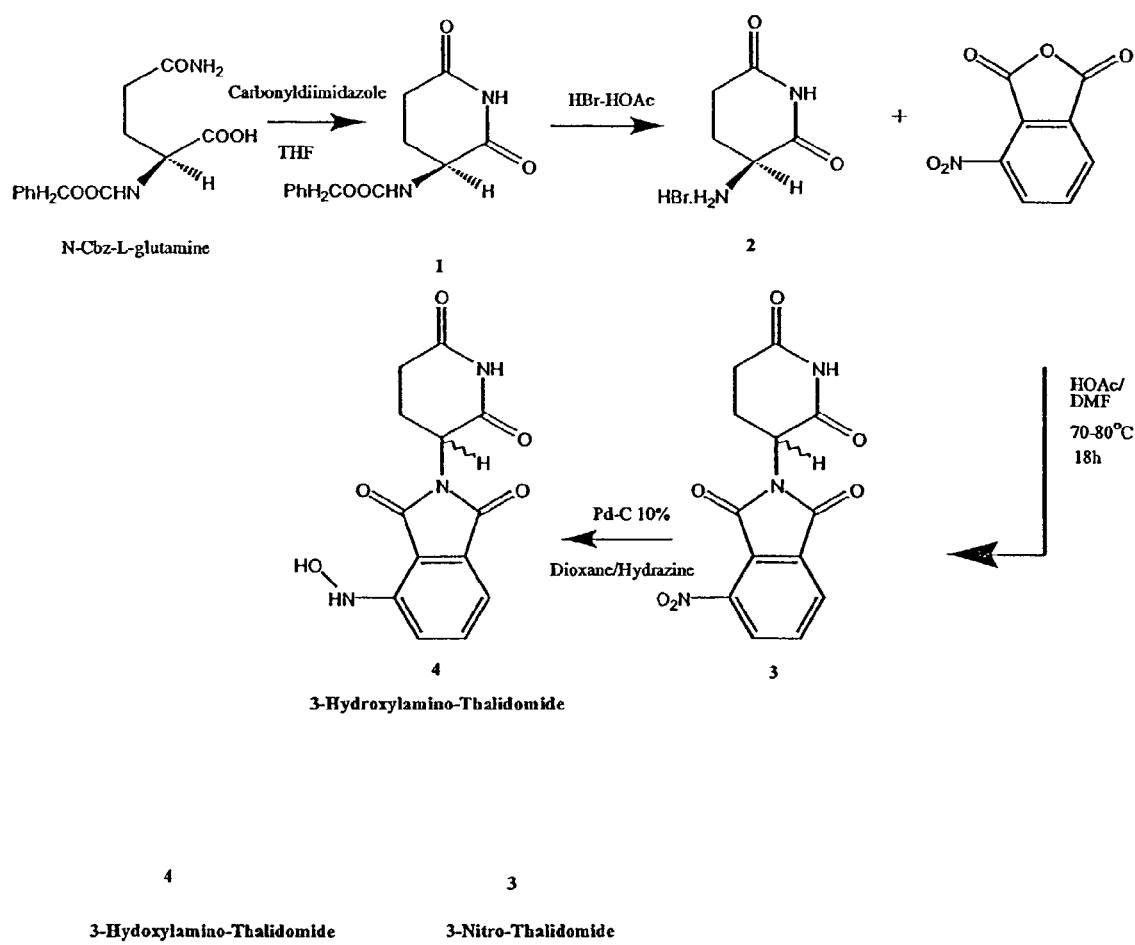
FIGS. 1 through 11 are synthesis models of representative compounds of the present invention.

The present invention includes compositions and methods for the treatment of diseases that are mediated by angiogenesis. The present invention also provides the synthesis of these compositions. One embodiment of the present invention is the use of nitrogen-substituted thalidomide analogs to inhibit unwanted angiogenesis. The present invention also includes compounds which cause dysmelia in the developing fetus and have anti-angiogenic activity. The present invention comprises a method of treating undesired angiogenesis in a human or animal comprising the steps of administering to the human or animal a composition comprising an effective amount of a teratogenic compound that is anti-angiogenic.

Thalidomide is the common name of 3-N-phthalimido-glutarimide, a molecule known to possess a wide variety of properties, including, reduction of TNF-alpha production, suppression of β-FGF-induced angiogenesis, and inhibition of tumor metastasis.

Analogs of thalidomide that can be used in accordance with the present invention include compounds included in the following general formulae. Examples of compounds that have anti-angiogenic properties are included within the following three formulae (A), (B) or (C):

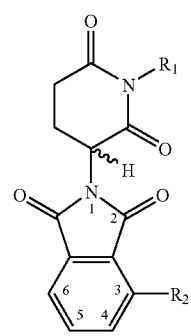

A)

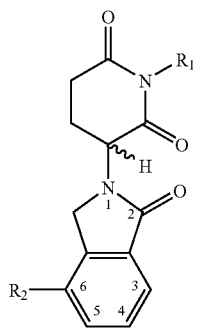

B)

-continued

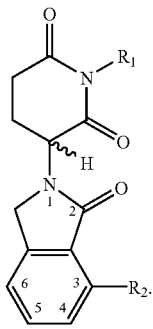

C)

In the above formulae A), B), and C):

R$_1$ can be independently selected from —H, —OH, —CH$_3$, —CH$_2$OZ (ethers), —CH$_2$OCOZ (esters), —CH$_2$OCONZ (carbamates), and —CH$_2$Z (alkyls), wherein Z is selected from H or —(CH$_2$)$_n$—H, where n is 1–10);

R$_2$ can be independently selected from —NH—NH$_2$ hydrazine), —NH—OH (hydroxalamine), —NH—OR$_3$, —N=N—R$_3$, —NH$_2$, —N(R$_3$)$_2$, —NHCOH, —NH-COCH$_3$, pyrazolidine, pyrazoline, tetrazole, imidazole, pyrazole, piprazine, and imidazoline; and R$_3$ can be independently selected from pyrazolidine, pyrazoline, tetrazole, imidazole, pyrazole, piprazine, and imidazoline.

Pyrazolidine, pyrazoline, tetrazole, piprazine, imidazole, pyrazole, and imidazoline have the following respective structures:

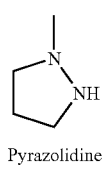

Pyrazolidine

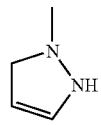

Pyrazoline

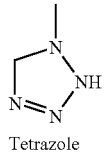

Tetrazole

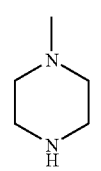

Piprazine

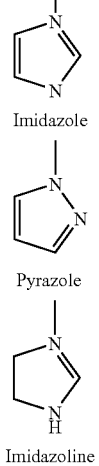

Imidazole

Pyrazole

Imidazoline

In an alternative embodiment, the present invention also includes di-substituted thalidomide analogs. Examples of compounds that have anti-angiogenic properties are included within the following general formula D):

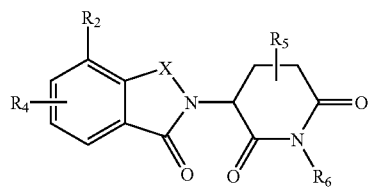

D)

wherein:

X is selected from

or —CH$_2$—;

R$_2$ is the same as defined above;

R$_4$, R$_5$, and R$_6$ may be the same or different and are selected from —NH$_2$, —OH, —CH$_3$, —H, —OCH$_3$, —O(CH$_2$)$_m$—H, where m is 1–7, —Cl, —Br, —F, —I, —CH$_2$OCONZ (carbamates), —CH$_2$Z (alkyls), —CH$_2$OZ (ethers), —CH$_2$OCOZ (esters), wherein Z is selected from H or —(CH$_2$)$_n$—H, where n is 1–10, —NH—NH$_2$ (hydrazine), —NH—OH (hydroxalamine), —NH—OR$_3$, —N=N—R$_3$, N(R$_3$)$_2$, —NHCOH, —NHCOCH$_3$, pyrazolidine, pyrazoline, tetrazole, imidazole, pyrazole, piprazine, and imidazoline.

In accordance with the present invention, any thalidomide analog within the scope of compounds of formula A), B), C), and D) may be employed in any combination with one another. Any combination of compounds of formula A) may be employed in the present invention. Likewise, any combination of compounds of formula B) may be employed in the present invention. Similarly, any combination of compounds of formula C) may be employed in the present invention. In addition, any combination of compounds of formula D) may be employed in the present invention.

In summary, the preferred compounds are nitrogen-substitutued thalidomide analogs that are teratogenic, and, more specifically, that cause dismelia. However, it is to be understood that it is not necessary for a compound to have both teratogenic activity and angiogenesis inhibiting activity to be considered part of the present invention. Dysmelia-causing compounds can be identified by the general procedures of Helm, Arzneimittle-forschung, 3 1(i/6):941–949 (1981), in which rabbit pups are examined after exposure to the compound in utero. The compounds can generally be purchased, e.g., from Andrulis Pharmaceuticals. Beltsville, Md., or synthesized according to known procedures. It is to be understood that the compounds of the present invention can exist as enantiomers and that the racemic mixture of enantiomers or the isolated enantiomers are all considered as within the scope of the present invention.

The tables below provide representative compounds of the thalidomide analogs of the present invention, while the Examples below provide the synthesis of representative compounds.

TABLE 1

Representative Compounds of the Present Invention According to Formulae A, B and C

| $R_1$ | $R_2$ | $R_3$ |
|---|---|---|
| —H | —NH—NH$_2$ | — |
| —OH | —NH—NH$_2$ | — |
| —CH$_3$ | —NH—NH$_2$ | — |
| ether | —NH—NH$_2$ | — |
| ester | —NH—NH$_2$ | — |
| carbamate | —NH—NH$_2$ | — |
| alkyl | —NH—NH$_2$ | — |
| —H | —NH—OR$_3$ | Pyrazolidine |
| —OH | —NH—OR$_3$ | Pyrazolidine |
| —H | —NH—OR$_3$ | Tetrazole |
| —OH | —NH—OR$_3$ | Tetrazole |
| —H | —NHCOH | — |
| —OH | —NHCOH | — |
| —H | —N(R$_3$)$_2$ | Pyrazolidine |
| —OH | —N(R$_3$)$_2$ | Pyrazolidine |
| —H | —N(R$_3$)$_2$ | Tetrazole |
| —OH | —N(R$_3$)$_2$ | Tetrazole |
| —H | Pyrazolidine | — |
| —OH | Pyrazolidine | — |
| —H | —N=N—R$_3$ | Pyrazolidine |
| —OH | —N=N—R$_3$ | Pyrazolidine |
| —H | —N=N—R$_3$ | Tetrazole |
| —OH | —N=N—R$_3$ | Tetrazole |
| —H | —NHCOCH$_3$ | — |
| —OH | —NHCOCH$_3$ | — |
| —H | —NH—OH | — |
| —OH | —NH—OH | — |
| —CH$_3$ | —NH—OH | — |
| ether | —NH—OH | — |
| ester | —NH—OH | — |
| carbamate | —NH—OH | — |
| alkyl | —NH—NH$_2$ | — |
| —OH | —NH$_2$ | — |
| —CH$_3$ | —NH$_2$ | — |
| ether | —NH$_2$ | — |
| ester | —NH$_2$ | — |
| carbamate | —NH$_2$ | — |
| alkyl | —NH$_2$ | — |
| —H | —N(R$_3$)$_2$ | Pyrazoline |
| —OH | —N(R$_3$)$_2$ | Pyrazoline |
| —H | Pyrazoline | — |
| —OH | Pyrazoline | — |
| —H | Tetrazole | — |
| —OH | Tetrazole | — |
| —H | —N=N—R$_3$ | Pyrazoline |
| —OH | —N=N—R$_3$ | Pyrazoline |

TABLE 1-continued

Representative Compounds of the Present Invention According to Formulae A, B and C

| $R_1$ | $R_2$ | $R_3$ |
|---|---|---|
| —H | —NH—OR$_3$ | Pyrazoline |
| —OH | —NH—OR$_3$ | Pyrazoline |
| —H | —NH$_2$CO | — |

However, Table 1 is not considered to be a complete list of compounds of the present invention according to formulae A), B), or C) and any possible combination of $R_1$, $R_2$ and $R_3$ as set forth previously and in conjunction with Table 1 is considered to be within the scope of the present invention.

TABLE 2

Representative Compound Of The Present Invention According To Formula D

| $R_2$ | $R_4$ | $R_5$ | $R_6$ |
|---|---|---|---|
| NH$_2$ | NH$_2$ | H | H |
| NH$_2$ | NH$_2$ | CH$_3$ | H |
| NH$_2$ | NH$_2$ | F | H |
| NH$_2$ | NH$_2$ | H | CH$_3$ |
| NH$_2$ | NHNH$_2$ | H | H |
| NH$_2$ | NHOH | H | H |
| NHNH$_2$ | NH$_2$ | H | H |
| NHNHOH | NH$_2$ | H | H |
| NH$_2$ | OH | H | H |
| NH$_2$ | OH | CH$_3$ | H |
| NH$_2$ | OH | F | H |
| NH$_2$ | OH | H | CH$_3$ |
| NH$_2$ | NH$_2$ | H | OH |

However, Table 2 is not considered to be a complete list of compounds of the present invention according to formula D) and any possible combination of $R_2$, $R_4$, $R_5$ and $R_6$ as set forth previously and in conjunction with Table 2 is considered to be within the scope of the present invention.

The following compounds are representative of the present invention:

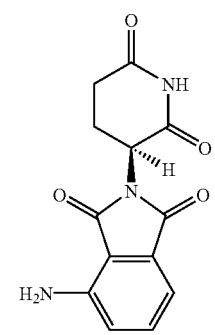

4
S(-)-3-amino-thalidomide

-continued
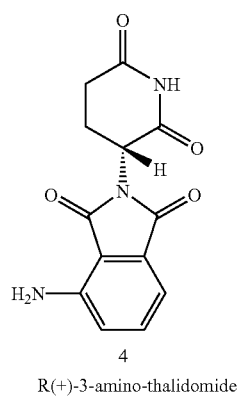
4
R(+)-3-amino-thalidomide
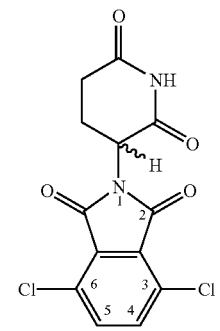
3, 6-Dichloro-thalidomide
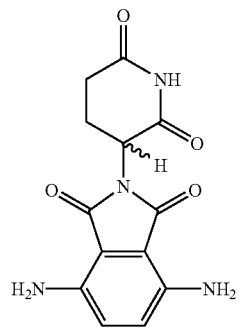
3, 6-Diamino-thalidomide
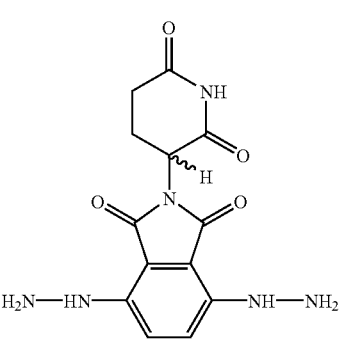
3, 6-Dihydrzino-thalidomide
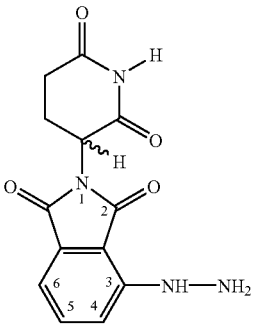
3-Hydrazino-Thalidomide
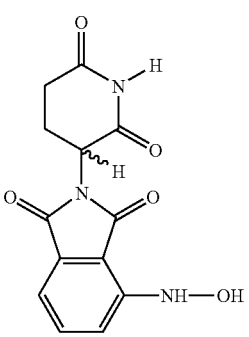
3-Hydroxylamino-Thalidomide
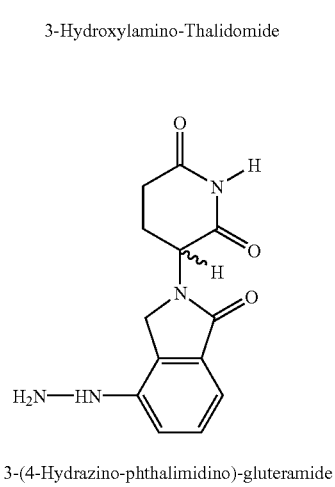
3-(4-Hydrazino-phthalimidino)-gluteramide
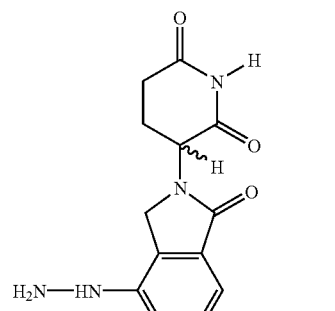
2-(4-amino-phthalimidino)-glutaric acid HCl -continued

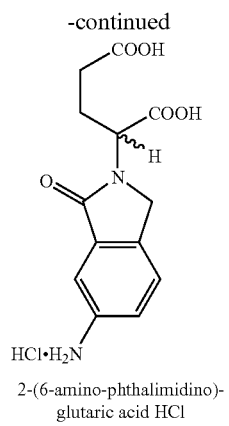
2-(6-amino-phthalimidino)-
glutaric acid HCl

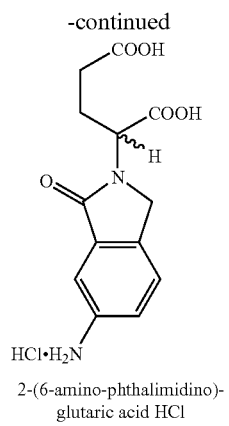
2-(7-amino-phthalimidino)-
glutaric acid HCl

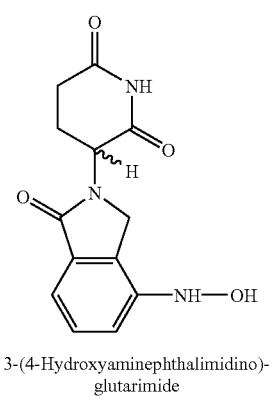
3-(4-Hydroxyaminephthalimidino)-
glutarimide

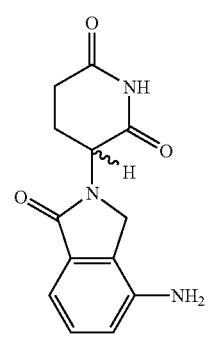
3-(4-amino-phthalimidino)-
glutarimide

-continued

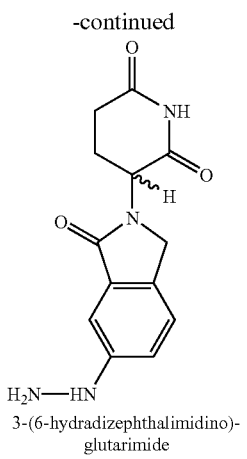
3-(6-hydradizephthalimidino)-
glutarimide

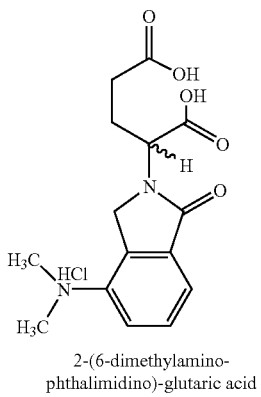
2-(6-dimethylamino-
phthalimidino)-glutaric acid

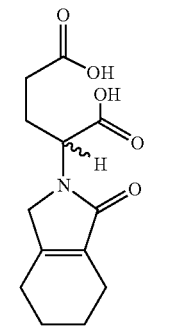
2-3,4,5,6-Tetrahydro-
phthalimidino)-glutaric acid

Further, thalidomide analogs in accordance with the present invention include, but are not limited to:

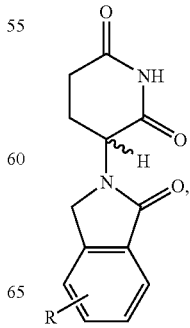

-continued

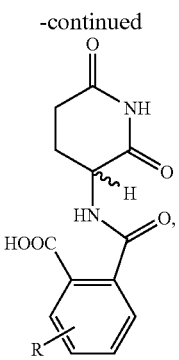

wherein R is selected from —NH—NH₂ (hydrazine), —NH—OH (hydroxalamine), —NH—OR₃, —N=N—R₃, —NH₂, —N(R₃)₂, —NHCOH, —NHCOCH₃, pyrazolidine, pyrazoline, tetrazole, imidazole, pyrazole, piprazine, and imidazoline, and R₃ is the same as defined above.

Figure 2:
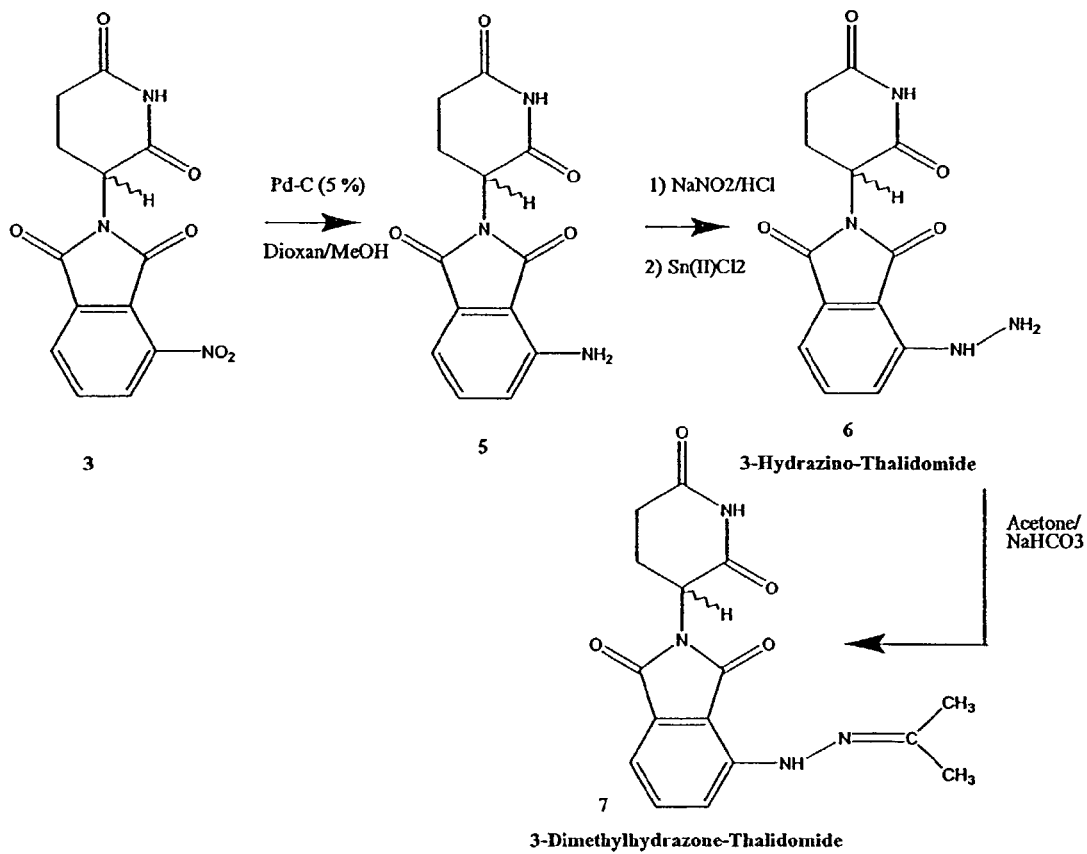
Figure 3:
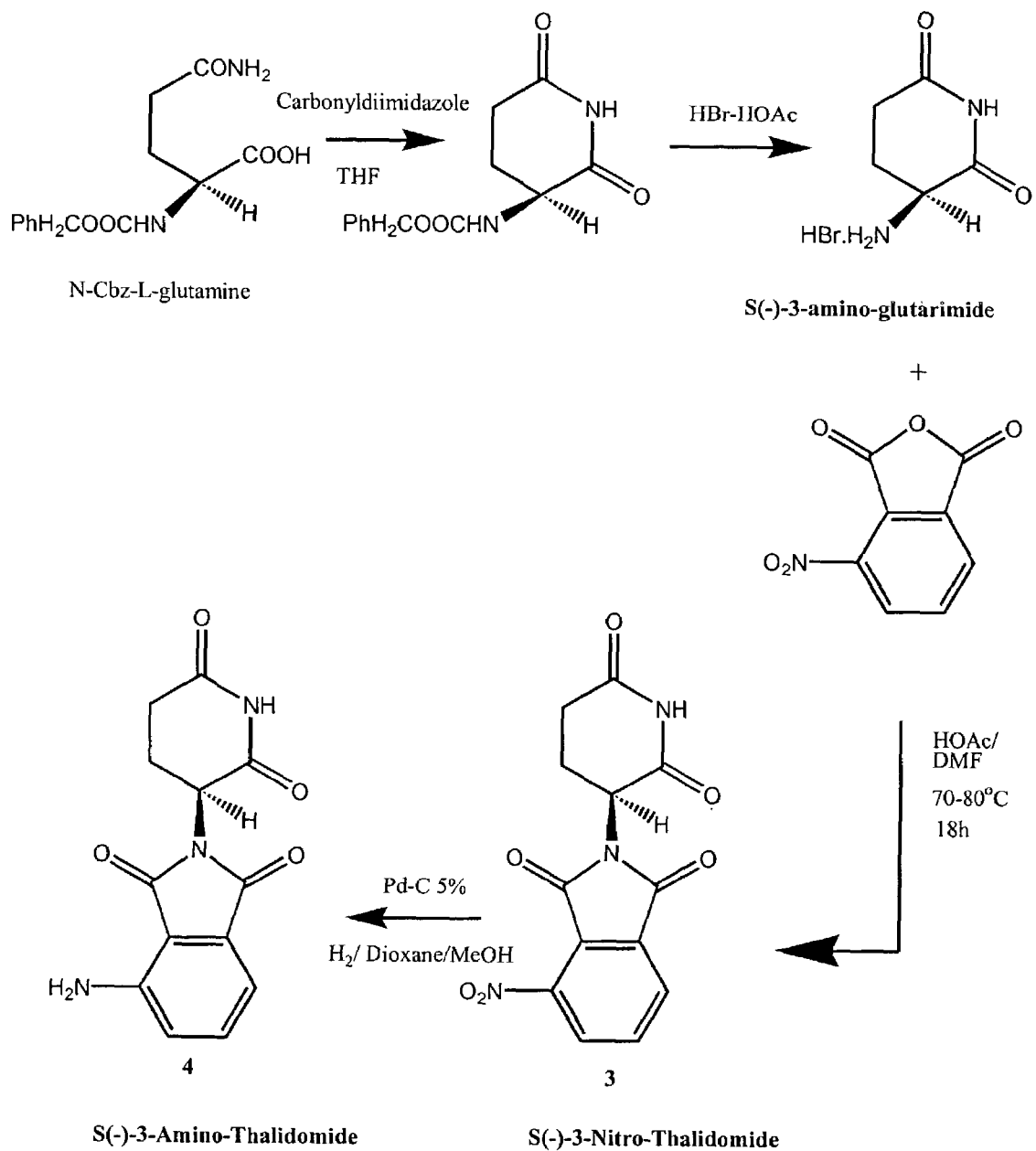

The present invention also includes the methods to synthesize the compounds of the present invention. As shown in FIGS. 1, 2 and 3, three representative compounds of the present invention, 3-hydazino-thalidomide, 3-hydroxylamino-thalidomide, and 3-4-diamino-thalidomide, were made. The synthesis processes for other compounds of the present invention are similar to the process generally described herein below for 3-hydazino-thalidomide, 3-hydoxylamino-thalidomide, and 3-4-diamino-thalidomide.

In FIGS. 1 and 2, the synthesis of 3-hydazino-thalidomide and 3-hydroxylamino-thalidomide is shown. First, N-carboxybenzyloxy-L-gluteramide (1) is synthesized. This is achieved by reacting, in a solvent, carboxybenzyloxy-L-glutamine and anhydrous, 1,1-carbonyldiiumidazole. Alternatively, carboxybenzyloxy-L-glutamine can be cyclized by N,N-Dicyclohexylcabdiimide in THF or in dichloromethane to carboxybenzyloxy-L-gluteramide. The reaction mixture is heated, desirably under reflux. The solvent, such as THF, is evaporated and the product is dissolved in another solvent, such as chloroform. The chloroform layer may then be washed with water and brine and dried over CaSO₄ anhydrous, filtered and evaporated to give a solid. The solid product is crystallized from ethyl ether to give a crystalline powder.

Next, 3-Amino-gluteramide.HBr (2) is synthesized. Into a solution of (1), an acid solution, such as a 30% HBr/acetic acid solution is added. The temperature of reaction mixture is desirably raised to room temperature and stirred. White solid powder of L-gluteramide HBr should appear in the reaction mixture. The solid is filtered and washed to give the product.

In the next step, (2) is mixed with DMF anhydrous and 3-nitrophthalic anhydride is added. After adding a solvent, such as acetic acid glacial, the reaction mixture is heated. Solvents are evaporated under vacuum to give a solid. Adding ethyl alcohol will form a powder. The solid product may then be separated and washed to form the 3-nitrotholidomide.

The 3-nitro-thalidomide is mixed with Pd/C and hydrazine hydrate is added and stirred, desirably at room temperature. The solvents are then evaporated and recryrstallized using methanol, or a similar compound, to form 3-hydroxylamino-thalidomide.

Or, the 3-nitro-thalidomide may be dissolved in a dioxane/methanol mixture, as shown in FIG. 3, and hydrogenated in the presence of Pd/C. After filtering the reaction mixture, the solvents are evaporated and recrystallized from ethyl acetate/dioxane to provide S(–)-3-amino-thalidomide.

The 3-Amino-thalidomide is then mixed in an acid, such as HCl, and water and mixed with sodium nitrite and stirred. Tin(II) chloride is added and the reaction mixture is stirred, desirably at room temperature. The solvents are evaporated and recryrstallized to give 3-hydrazino-thalidomide-HCl salt. The free base of 3-hydrazino-thalidomide is prepared by dissolving the product in a solvent, such as acetone, and then passing it over dry sodium bicarbonate. After evaporating the acetone the product is recrystallized from absolute ethanol to give 3-hydrazino-thalidomide.

Figure 4:
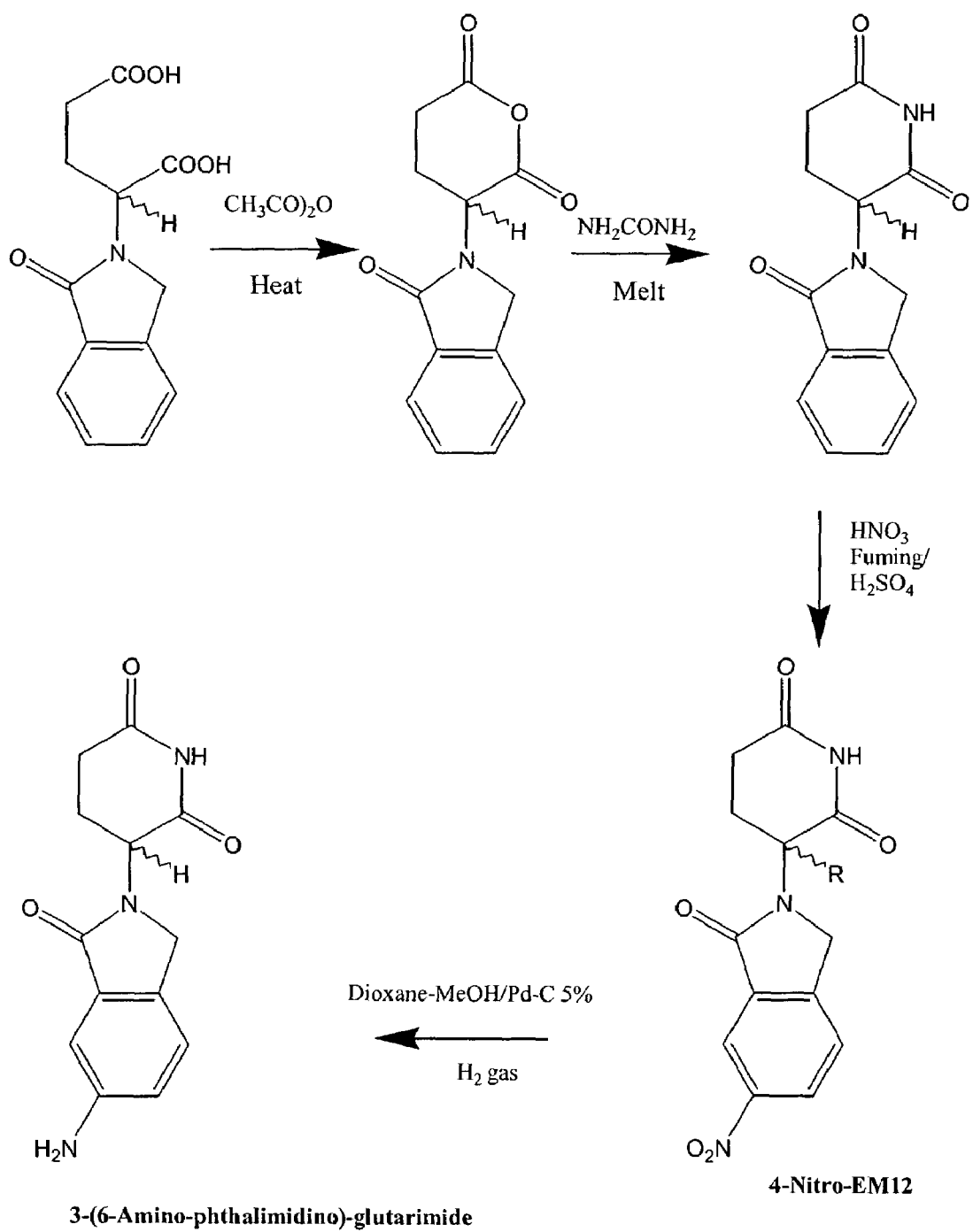
Figure 5:
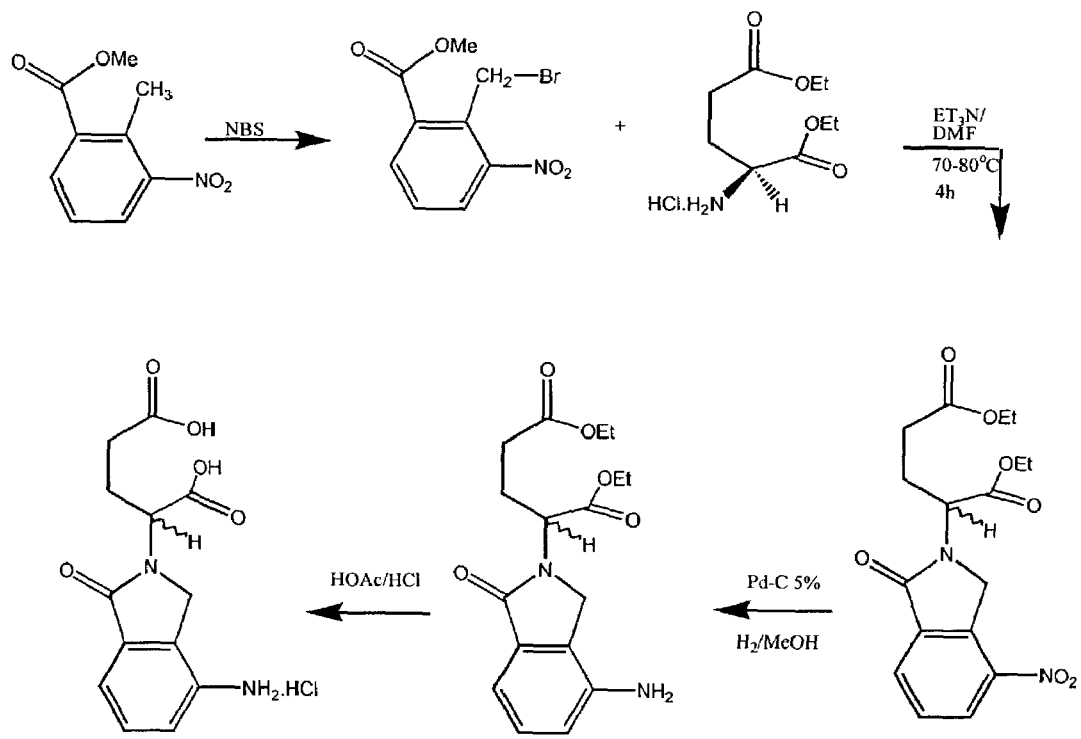
Figure 6:
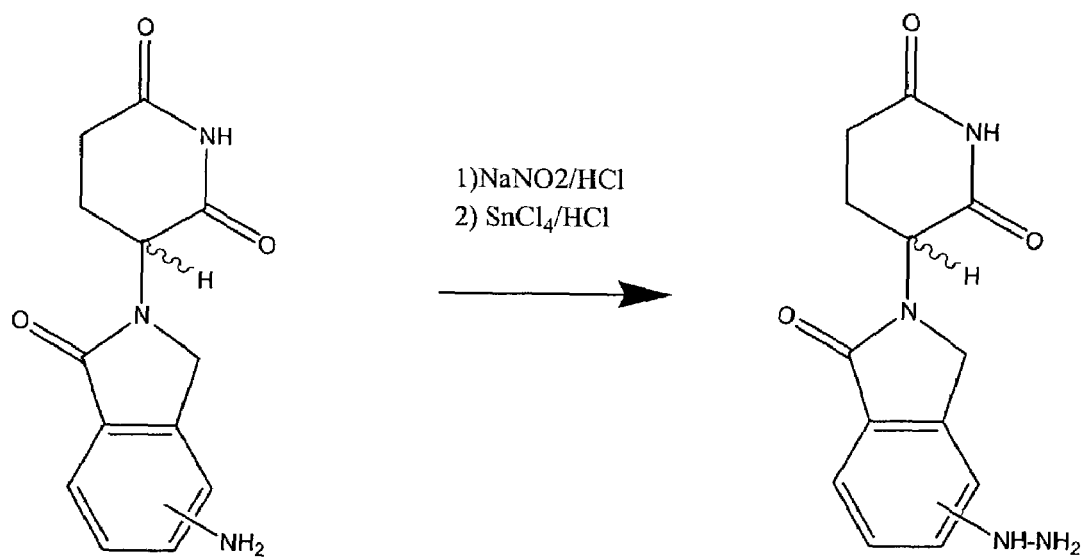
Figure 7:
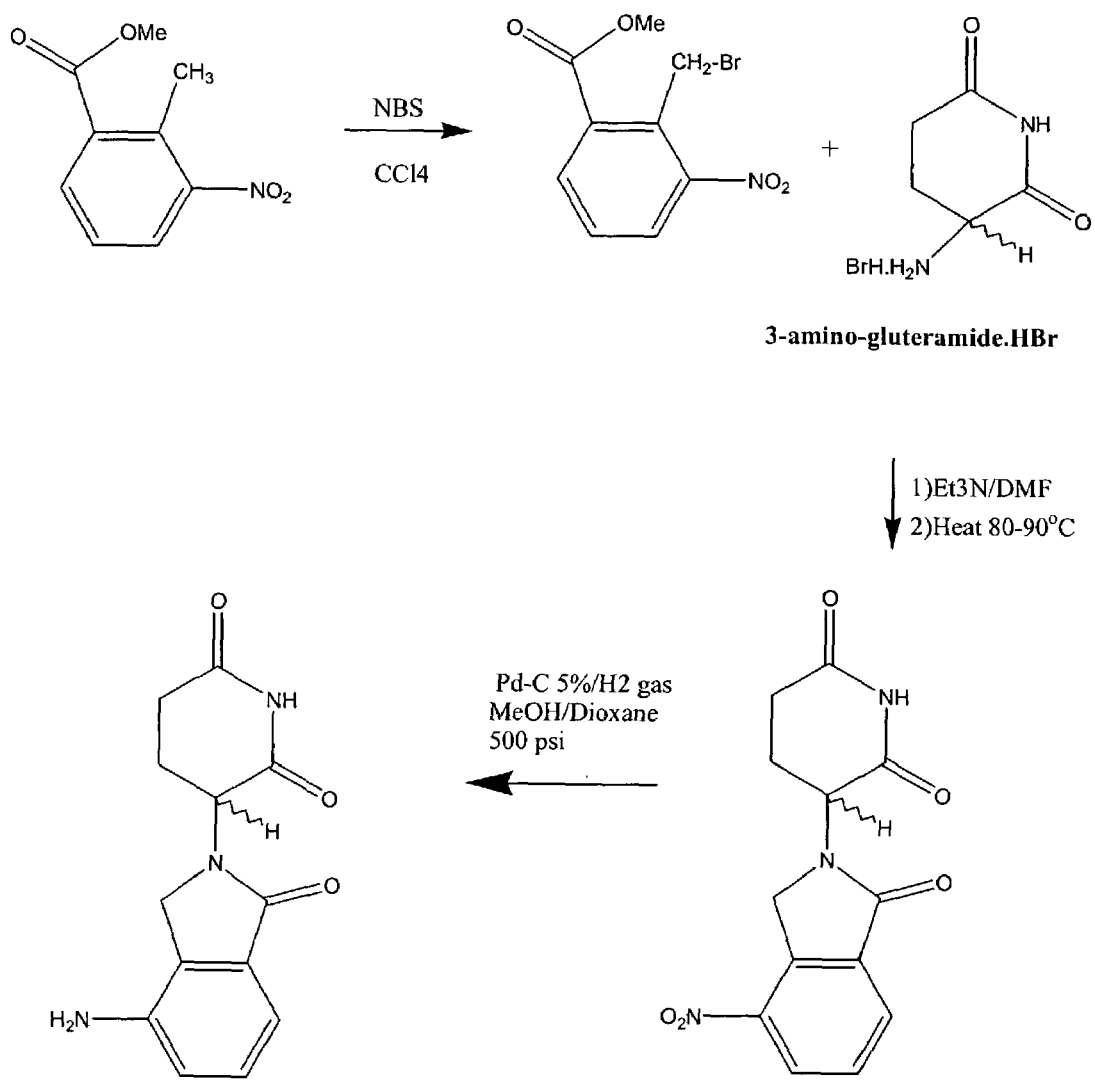
Figure 8:
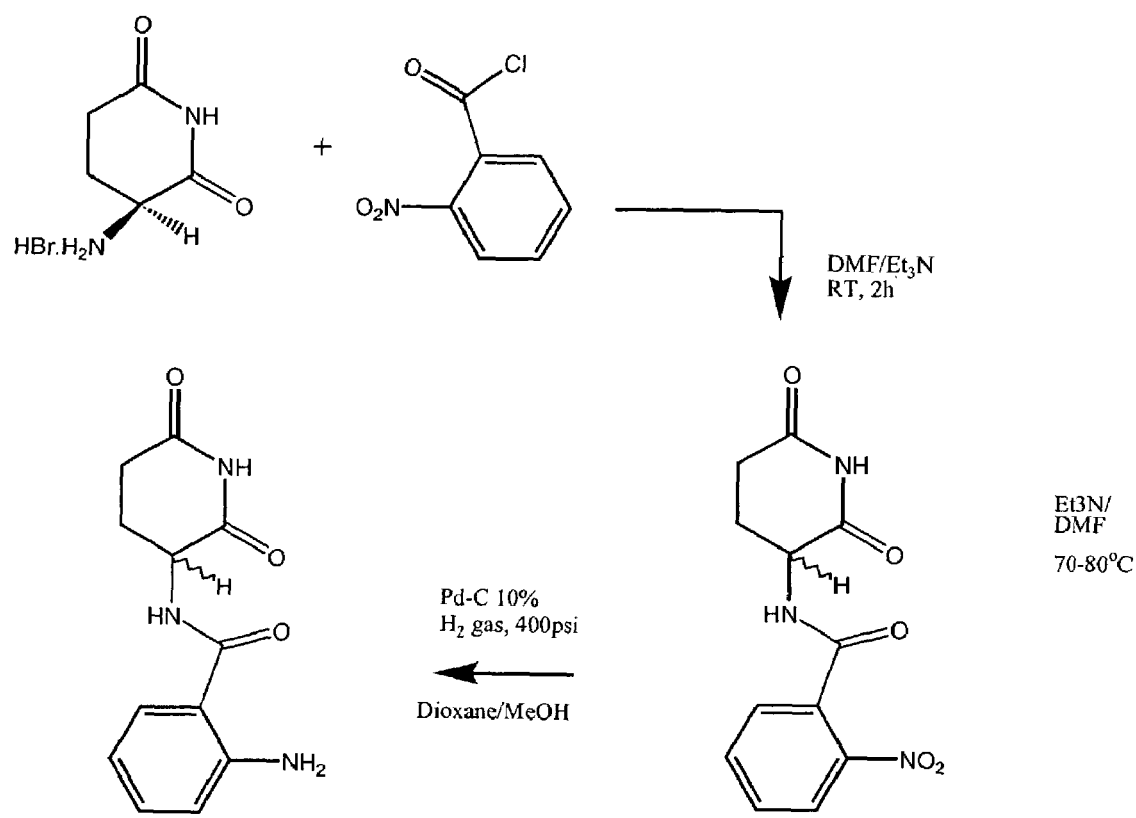

FIGS. 4 through 8 provide synthesis schemes for compounds in accordance with the present invention. These schemes are discussed in detail in the examples below. FIG. 4 illustrates the synthesis of 4-nitro-EM12 and 3-(6-aminophthalimidino)-gluterimide. FIG. 5 illustrates the synthesis of 3-(4-aminophthalimidino)-glutaric acid.HCl. FIG. 6 illustrates the synthesis of 4, 6 or 7,3-(hydrazino-phthalimidino)-gluteramide. FIG. 7 illustrates the synthesis of 3-(4-aminophthalimidino)-gluteramide. FIG. 8 illustrates the synthesis of 3-(2-aminobenzoylamido)-gluteramide.

Figure 9:
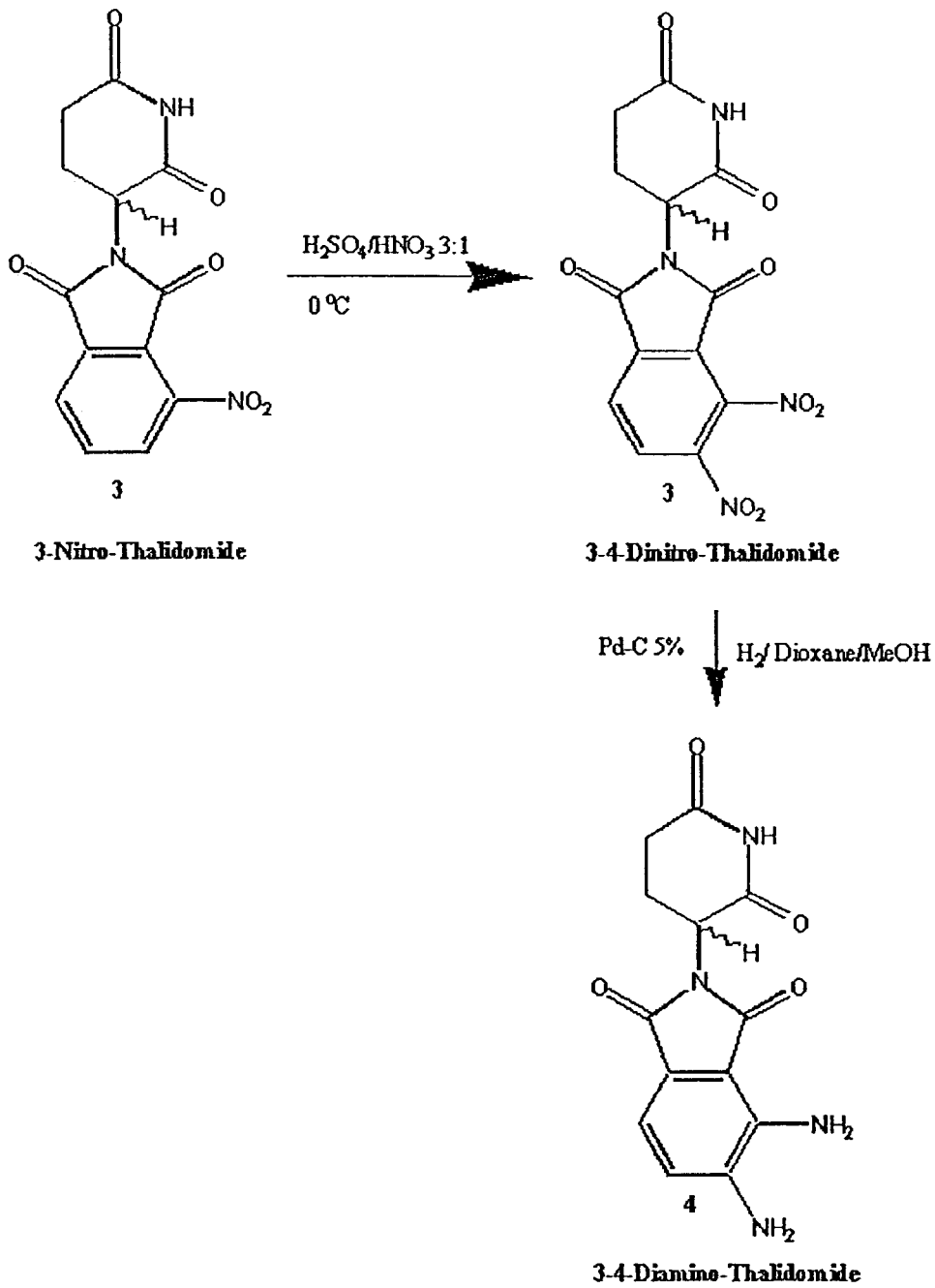

In FIG. 9, the synthesis of 3-4-diamino-thalidomide is shown. First, 3-nitro-thalidomide is reacted in the presence of an acid mixture, such as 3:1 sulfuric acid/nitric acid, to form 3-4-dinitro-thalidomide. Then, the –4-dinitro-thalidomide is reacted in the presence of a catalyst, such as Pd-C 5%, hydrogen, dioxane, and methanol to form the 3–4-diamino-thalidomide.

Figure 10:
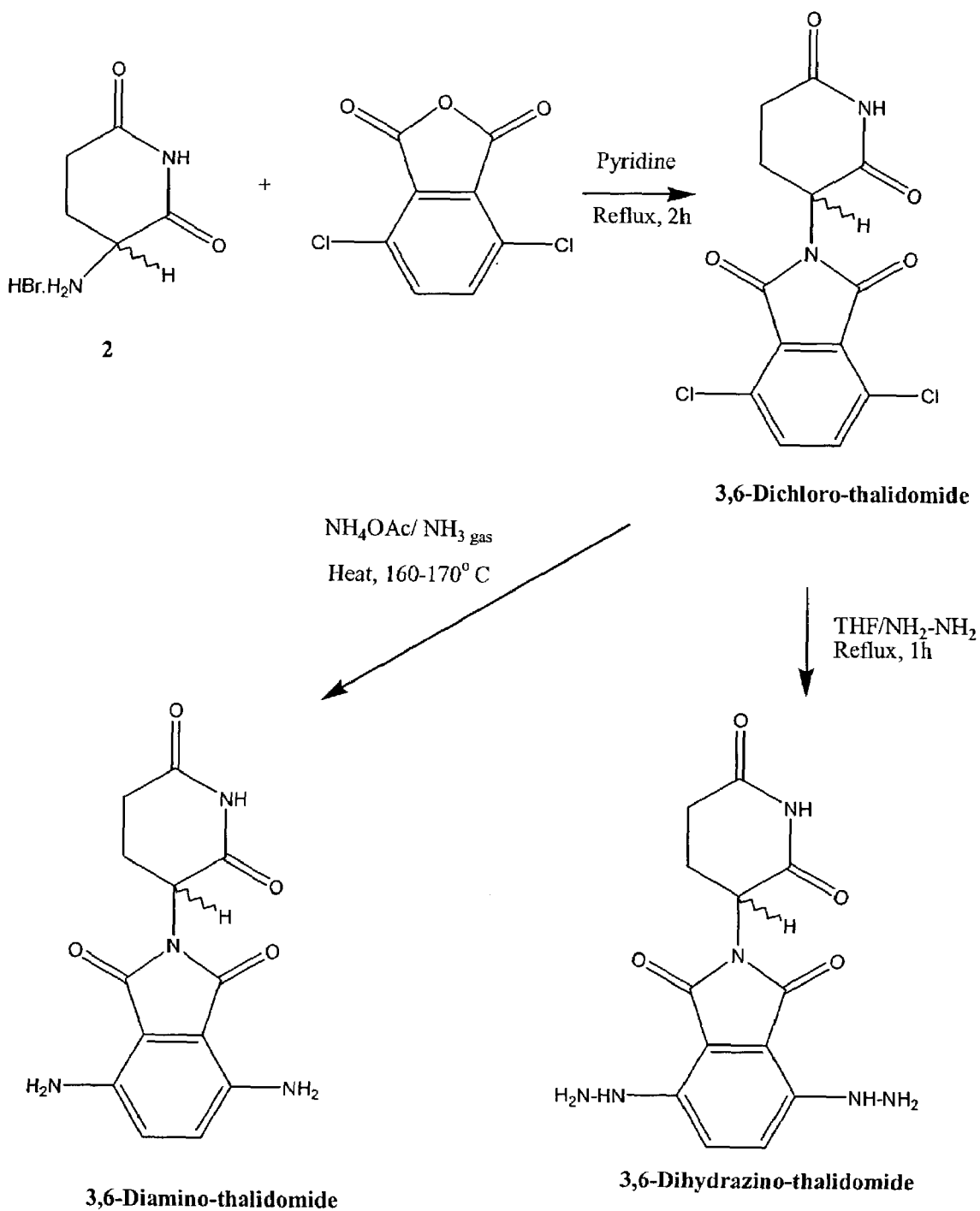
Figure 11:
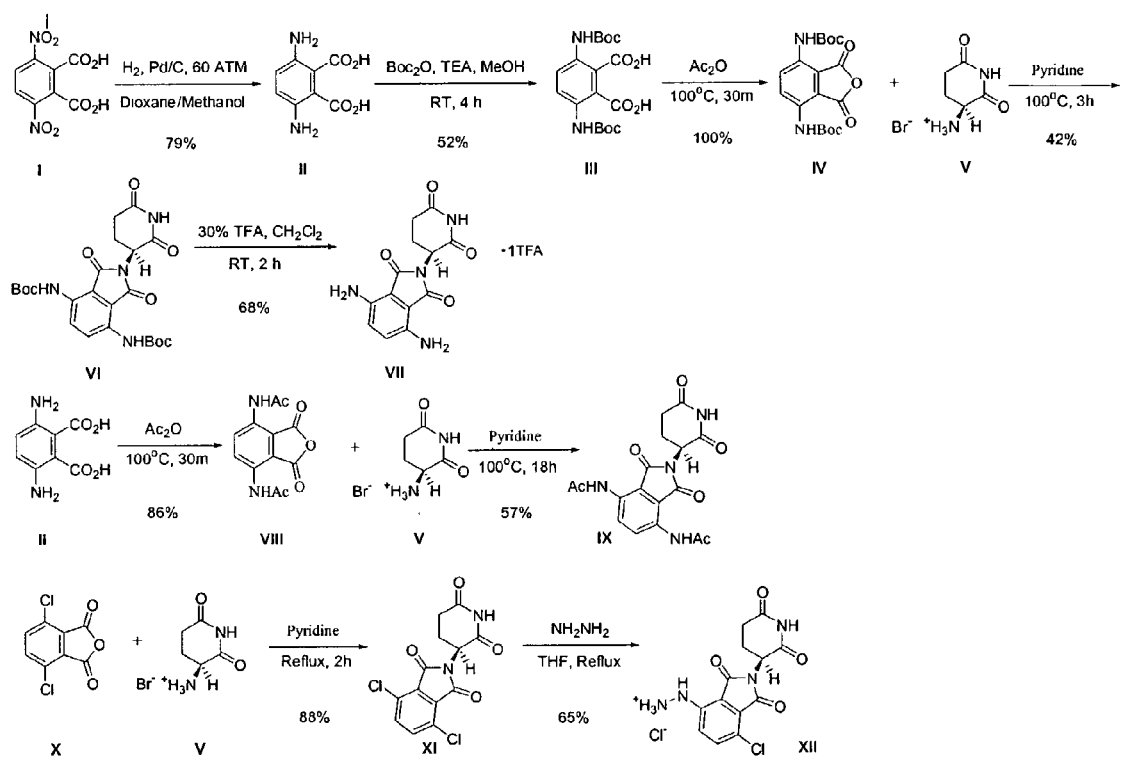

FIG. 10 illustrates the synthesis of 3,6-diamino-thalidomide and 3,6-dihydrazion-thalidomide. FIG. 11 illustrates the synthesis of the compounds discussed in Examples 37–45. Specifically, FIG. 11 provides the reaction scheme for 3-hydrazino-6-chloro-thalidomide-HCl.

The compounds described above can be provided as pharmaceutically acceptable formulations using formulation methods known to those of ordinary skill in the art. These formulations can be administered by standard routes. In general, the combinations may be administered by the topical, transdermal, oral, rectal or parenteral (e.g., intravenous, subcutaneous or intramuscular) route. In addition, the combinations may be incorporated into biodegradable polymers allowing for sustained release of the compound, the polymers being implanted in the vicinity of where drug delivery is desired, for example, at the site of a tumor. The biodegradable polymers and their use are described, for example, in detail in Brem et al., *J. Neurosurg.* 74:441–446 (1991).

The dosage of the compound will depend on the condition being treated, the particular compound, and other clinical factors such as weight and condition of the human or animal and the route of administration of the compound. It is to be understood that the present invention has application for both human and veterinary use. For oral administration to humans, a dosage of between approximately 0.1 to 300 mg/kg/day, preferably between approximately 0.5 and 50 mg/kg/day, and most preferably between approximately 1 to 10 mg/kg/day, is generally sufficient.

The formulations include those suitable for oral, rectal, ophthalmic, (including intravitreal or intracameral) nasal, topical (including buccal and sublingual), vaginal or parenteral (including subcutaneous, intramuscular, intravenous, intradermal, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into associate the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tamports, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of the present invention may include other agents conventional in the art having regard to the type of formulation in question, for example, those suitable for oral administration may include flavoring agents.

Diseases associated with corneal neovascularization that can be treated according to the present invention include but are not limited to, diabetic retinopathy, retinopathy of prematurity, corneal graft rejection, neovascular glaucoma and retrolental fibroplasias, epidemic keratoconjunctivitis, Vitamin A deficiency, contact lens overwear, atopic keratitis, superior limbic keratitis, pterygium keratitis sicca, Sjogren's disease, acne, rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi's sarcoma, Mooren's ulcer, Terrien's marginal degeneration, mariginal keratolysis, trauma, rheumatoid arthritis, systemic lupus, polyarteritis, Wegener's syndrome, sarcoidosis, scleritis, Stevens-Johnson's disease, pemphigoid, radial keratotomy, and corneal graph rejection.

Diseases associated with retinal/choroidal neovascularization that can be treated according to the present invention include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eales' disease, Behcet's disease, infections causing a retinitis or choroiditis, presumed ocular histoplasmosis, Best's disease, myopia, optic pits, Stargart's disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreoretinopathy, whether or not associated with diabetes.

Another disease which can be treated according to the present invention is rheumatoid arthritis. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Another disease that can be treated according to the present invention are hemangiomas, Osler-Weber-Rendu disease, or hereditary hemorrhagic telangiectasia, solid or blood borne tumors and acquired immune deficiency syndrome.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

Synthesis of 3-hydazino-thalidomide and 3-hydoxylamino-thalidomide: 3-hydoxylamino-thalidomide 3-hydazino-thalidomide was synthesized as depicted in FIGS. 1 and 2.

First, N-carboxybenzyloxy-L-gluteramide (1) was synthesized. Synthesis of N-carboxybenzyloxy-L-gluteramide (1): Into a stirring solution of carboxybenzyloxy-L-glutamine (2.8 g, 10 mmols) in 40 mL THF anhydrous, 1,1-carbonyldiimidazole (1.92 g, 12 mmols) was added. (Alternatively, carboxybenzyloxy-L-glutamine can be cyclized by N,N-Dicyclohexylcabdiimide in THF or in dichloromethane to carboxybenzyloxy-L-gluteramide). The reaction mixture was heated under reflux for 18 hours. The THF was evaporated and the product was dissolved in chloroform. The chloroform layer was washed with water and brine and dried over $CaSO_4$ anhydrous, filtered and evaporated to give white solid. The solid product was crystallized from ethyl ether to give 2.4 grams crystalline powder (90%). 1H NMR in CDCl3 confirmed the product as carboxybenzyloxy-L-gluteramide.

Next, 3-Amino-gluteramide.HBr (2) was synthesized. Synthesis of 3-Amino-gluteramide.HBr (2): Into a solution of 1(1.2 g, 4.6 mmols) in 15 mL acetic acid glacial, 8 mL of 30% HBr/acetic acid solution was added at 20° C. The temperature of reaction mixture was raised to RT and stirred for 1 hour. White solid powder of L-gluteramide HBr started appearing in reaction mixture. The solid was filtered and washed with 5 mL acetic acid glacial and then with ether to give 1.8 g (80%) product. Analysis on Polarimeter of product (2) showed (−) rotation, $[a]^{25}_D$ (c=1, water)=−37.5° and confirmed the product as S(−)-3-amino-gluteramide. 1H NMR in DMSO-D6 confirmed the product as 3-amino-L-gluteramide HBr.

In the next step, 3-Nitro-thalidomide (3) was synthesized. Synthesis of 3-Nitro-thalidomide (3): Into a solution of (4.18 g, 20 mmols) 2 amino-gluteramide-HBr in 50 mL of DMF anhydrous 3.8 g (20 mmols) 3-nitrophthalic anhydride was added. After adding 100 mL acetic acid glacial, reaction mixture was heated at 70–80° C. for 24 hours. Solvents were evaporated under vacuum to give light brown solid. On adding 10 mL ethyl alcohol, light brown powder was formed. The solid product was separated and washed with 20 mL ethyl alcohol. 1H NMR in DMSO-D6 confirmed the product as 3-nitro-tholidomide.

The next step involved the synthesis of 3-hydoxylamino-thalidomide (4). Synthesis of 3-hydoxylamino-thalidomide (4): In to a solution of 3-nitro-thalidomide (337 mg, 1.0 mmols) in 50 mL dioxane, with Pd/C 10% (100 mg) was added slowly 100 μl (2 mmol) of hydrazine hydrate and the reaction mixture was stirred for 18 hours at room temperature. After filtering the reaction mixture through Celite filtering agent the solvents were evaporated to give yellow powder. The product was recryrstallized from hot methanol to afford 290 mg (85%) of 3-hydoxylamino-thalidomide. 1H NMR in DMSO-D6 confirmed the product as 3-hydroxylamino-thalidomide.

Then, S-(−)-3-Amino-thalidomide (5) was synthesized. Synthesis of S-(−)-3-Amino-thalidomide (5): 3-nitro-thalidomide (1 g, 3.3 mmols) was dissolved in 50 mL dixona/methanol 4:1 mixture and hydrogenated in Parr hydrogenater at 40 psi of hydrogen in the presence of Pd/C 5% for 4 hours. After filtering the reaction mixture through Celite filtering agent the solvents were evaporated under vacuum to give yellow powder. The product was recrystallized from ethyl acetate/dioxane to afford 800 mg (85%) of S(−)-3-amino-thalidomide. 1H NMR in DMSO-D6 confirmed the product as S-(−) 3-amino-thalidomide. Absolute configuration was determined by comparison of specific rotation $[a]^{25}_D$ of R- and S-3-amino-thalidomide to the analogous compounds R-(+)- and S-(−)-thalidomide, which has been previously determined on the resolved enantiomers. Analysis on polarimeter of product (5) showed (−) rotation.

Finally, 3-Hydrazino-thalidomide (6) was synthesized. Synthesis of 3-Hydrazino-thalidomide (6): In to a solution of 3-Amino-thalidomide (270 mg, 1.0 mmols) in 12 mL HCL (conc)/water 2:1 mixture sodium nitrite (80 mg, 2.2 mmol) in 2 mL water was added at 0° C. and stirred for 20 min. After adding Tin(II) chloride (556 mg, 3 mmol) at 0° C. the reaction mixture was stirred for 1 hour at RT. After 1 hour the solvents were evaporated under vacuum to give yellow powder. The product was recryrstallized from isopropanol to afford 300 mg (85%) of 3-hydrazino-thalidomide-HCl salt. The free base of 3-hydrazino-thalidomide was prepared by dissolving the product in Acetone and then passing it over dry sodium bicarbonate. After evaporating acetone the product was recrystallized from absolute ethanol. 1H NMR in DMSO-D6 confirmed the product as 3-hydrazino-thalidomide.

The following compounds were synthesized by modification in methods described in; Shealy et. al. *J. Pharm. Sci.*, 1968, 57, 757–764; Polonski, et. al. *J. Chem. Soc. Perkin Trans. I*, 1988, 639–648; Muller et. al. *Bioorg. Med. Chem. Lett.* 1999, 9, 1625–1630; Almansa et. al. *J. Med. Chem.* 1993, 36, 2121–2133; Helm, et. al. *Arzneim-Forsch./Drug Res.* 1981, 31, 941–949; Shah et. al. *J. Med. Chem.* 1999, 42, 3014–3017; Menard et. al. *Can. J. Chem.* 1963, 41, 1722–1725; Egbertson et. al. *Bioorg. Med. Chem. Lett.* 1994, 4, 1835–1840, which are all incorporated herein by reference. Further, in the following examples, room temperature (RT) is about 25° C.

Example 2

Synthesis of S-(−)-(3-benzyloxycarbonylamino)-glutarimide: Into a stirring solution of carboxybenzyloxy-L-glutamine (2.8 g, 10 mmols) in 40 mL THF anhydrous, 1,1-carbonyldiimidazole (1.92 g, 12 mmols) were added. The reaction mixture was heated under reflux for 18 hours. The THF was evaporated and the product was dissolved in chloroform. The chloroform layer was washed with water and brine and dried over $CaSO_4$ anhydrous, filtered and evaporated to give white solid. The solid product was crystallized from ethyl ether to give 2.4 grams crystalline powder (90%). Alternatively, carboxybenzyloxy-L-glutamine can be cyclized by treating with $SOCl_2$ in DMF at about −70° C. to about 0° C. for 1 hour to S-(−)-(3-benzyloxycarbonylamino)-glutarimide. The reaction mixture was diluted with $CHCl_3$ and washed with 5% $Na_2CO_3$, dried over $Na_2SO_4$ anhydrous, filtered, and evaporated to give 2.5 g (90%) S-(−)-(3-benzyloxycarbonylamino)-glutarimide). $^1H$ NMR in $CDCl_3$ confirmed the product as S-(−)-(3-benzyloxycarbonylamino)-glutarimide. 1H NMR ($CDCL_3$, PPM), 8.2 (1H, s broad), 7.4 (5H, s, aromatic), 5.8 (1H, d), 5.15 (2H, s), 4.4 (1H, dd, J=4.5, 3), 2.95–2.4 (3H, m), 1.86 (1H, d, t, J=11.5, 6.5). m. p. 122–124° C. (lit=122–124° C.).

Example 3

Synthesis of S-(−)-3-Amino-glutarimide.HBr: Into a solution of S-(−)-(3-benzyloxycarbonylamino)-glutarimide (1.2 g, 4.6 mmols) in 15 mL acetic acid glacial, 8 mL of 30% HBr/acetic acid solution was added at 20° C. The temperature of reaction mixture was raised to RT and stirred for 1 hour. White solid powder of S-(−)-2-Amino-gluteramide-.HBr started appearing in the reaction mixture. The solid was filtered and washed with 5 mL acetic acid glacial and then with ether to give 1.8 g (80%) product. Analysis on polarimeter of product showed (−) rotation, $[a]^{25}_D$ (c=1, water)= −37.5° and confirmed the product as S(−)-2-amino-gluteramide. 1H NMR in DMSO-$D_6$ confirmed the product as 2-amino-L-gluteramide.HBr. 1H NMR (DMSO-$D_6$, PPM), 11.60 (1H, s broad), 8.45 (3H, s broad), 4.4 (1H, dd, J=4.5, 3), 2.85–2.45 (2H, m), 2.25–1.90 (2H, m), m. p. 279–281° C. (lit=279° C.).

Example 4

Synthesis of S(−)-3-Nitro-thalidomide: Into a solution of (4.18 g, 20 mmols) 3-amino-gluteramide-HBr in 50 mL of DMF anhydrous 3.8 g (20 mmols) 3-nitrophthalic anhydride was added. After adding 100 mL acetic acid glacial, reaction mixture was heated at about 70–80° C. for about 24 hours. Solvents were evaporated under vacuum to give off-white solid. On adding 10 mL ethyl alcohol, off-white powder was formed. The solid product was separated and washed with 20 mL ethyl alcohol. 1H NMR in DMSO-D6 confirmed the product as S(−)-3-nitro-tholidomide. m. p. 228–229° C. (lit=228.5–229.5° C.). 1H NMR (DMSO-$D_6$, PPM), 11.25 (1H, s broad), 8.35 (1H, d, J=7.2), 8.25 (1H, d, J=7.0), 8.15 (1H, t, J=8.0), 5.2 (1H, dd, J=5.5, 7.2), 3.00–2.85 (1H, m), 2.65–2.4 (2H, m), 2.15–2.05 (1H, m).

Example 5

Synthesis of S-(−)-3-Amino-thalidomide: 3-nitro-thalidomide (1 g, 3.3 mmols) was dissolved in 50 mL dioxane/methanol 4:1 mixture and hydrogenated in a Parr hydrogenater at 40 psi of hydrogen in the presence of Pd/C 5% for about 4 hours. After filtering the reaction mixture through Celite filtering agent the solvents were evaporated under vacuum to give yellow powder. Alternatively S(−)-3-amino-thalidomide can be synthesized by dissolving the of S(−)-3-nitro-thalidomide in conc. HCl and treated the reaction mixture with granulated tin. After heating the reaction mixture at about 70–80° C. for about 2 hours, it was filtered and acid evaporated under reduced pressure. The product was recryrstallized from water and then ethyl acetate/dioxane to afford 800 mg (85%) of S(−)-3-amino-thalidomide. 1H NMR in DMSO-$D_6$ confirmed the product as S-(−)-3-amino-thalidomide. m. p. 318.2–319.5° C. 1H NMR (DMSO-$D_6$, PPM), 11.10 (1H, s broad), 7.45 (1H, t, J=7.5), 7.05 (1H, d, J=5.2), 6.95 (1H, d, J=5.2), 6.5 (2H, s broad), 5.05 (1H, dd, J=5.0, 13.42), 2.95–2.80 (1H, m), 2.65–2.5 (2H, m), 2.05–1.95 (1H, m). Absolute configuration was determined by comparison of specific rotation $[a]^{25}_D$ of R- and S-3-amino-thalidomide to the analogous compounds R(+)- and S(−)-thalidomide, which had been previously determined on the resolved enantiomers. Analysis on polarimeter of product showed (−) rotation, $[a]^{25}_D$ (C=0.5, dioxanel)=−27.7.0° and confirmed the product as S(−)-3-amino-thalidomide.

The two enanteomers of 3-amino-thalidomide were resolved by chiral HPLC column Welk-01 (10 mm×750 mm) and eluted with CH3CN/MeOH/H2O 1:1:5 mixture. The retention time for S(+) isomer was 33.74 min and for R (+) isomer 35.62 respectively at a flow rate of 2 mL/min at 240 nm (FIG. 1).

Example 6

Synthesis of R-(+)-3-amino-thalidomide: Compound R-(+)-3-Amino-thalidomide was synthesized by the same procedure as for S-(−)-3-Amino-thalidomide, except the synthesis was started with commercially available carboxybenzyloxy-D-glutamine. Analysis on a polarimeter of product showed (+) rotation $[a]^{25}_D$ (c=1, dioxanesl)=+37.0° and confirmed the product as R(+)-3-amino-thalidomide. 1H NMR in DMSO-$D_6$ confirmed the product as 3-amino-thalidomide.

Example 7

Synthesis of 3-hydoxylamino-thalidomide: Into a solution of 3-nitro-thalidomide (337 mg, 1.0 mmols) in 50 mL dioxane, with Pd/C 10% (100 mg) was added slowly 100 ul (2 mmol) of hydrazine hydrate and the reaction mixture was stirred for about 18 hours at room temperature. After filtering the reaction mixture through Celite filtering agent the solvents were evaporated to give yellow powder. The product was recryrstallized from hot methanol to afford 290 mg (85%) of 3-hydoxylamino-thalidomide. 1H NMR in DMSO-$D_6$ confirmed the product as 3-hydroxylamino-thalidomide. 1H NMR (DMSO-$D_6$, PPM), 10.85 (1H, s broad), 9.5(1H, s broad), 8.65(1H, d J=13.5, NH—OH), 8.25 (1H, d, J=7.3), 7.95 (1H, d, J=5.2), 7.65 (1H, t, J=7.2), 6.5 (2H, s broad), 4.75 (1H, dd, J=5.0, 13.42), 2.78–2.50 (1H, m), 2.55–2.50 (1H, m), 2.05–1.95 (2H, m).

Example 8

Synthesis of 3-Hydrazino-thalidomide: Into a solution of 3-Amino-thalidomide (270 mg, 1.0 mmols) in 12 mL HCL (conc)/water 2:1 mixture sodium nitrite (80 mg, 2.2 mmol) in 2 mL water was added at about 0° C. and stirred for about 10 min. After adding Tin(II) chloride (556 mg, 3 mmol) at 0° C., the reaction mixture was stirred for about 1 hour at RT. After about 1 hour the solvents were evaporated under vacuum to give yellow powder. The product was recryrstallized from isopropanol to afford 300 mg (85%) of 3-hydrazino-thalidomide-HCl salt. The free base of 3-hydrazino-thalidomide was prepared by dissolving the product into Acetone and then passing it over dry sodium bicarbonate. After evaporating the acetone, the product was recrystallized from water. 1H NMR in DMSO-$D_6$ confirmed the product as 3-hydrazino-thalidomide. 1H NMR (DMSO-$D_6$, PPM), 11.05 (1H, s broad), 9.05(1H, s broad), 7.85 (2H, m), 7.25 (1H, d, J=3.2), 5.10 (1H, dd, J=5.2, 13.2), 2.95–2.80 (1H, m), 2.70–2.50 (2H, m), 2.10–1.95 (1H, m), 1.90 (2H, s).

Example 9

Synthesis of 3,6-dichloro-thalidomide: Into a solution of (4.18 g, 20 mmols) 2 amino-gluteramide-HBr in 50 mL of pyridine anhydrous 3.3 g (20 mmols) 3, 6-dichlorophthalic anhydride was added. The reaction mixture was heated at about 70–80° C. for about 4 hours. Solvents were evaporated under vacuum to give a light brown solid. On adding 10 mL water, white powder was formed. The solid product was separated and washed with 20 mL water and recystalized from MeOH. 1H NMR in DMSO-D6 confirmed the product as 3,6-dichlorotholidomide. 1H NMR (DMSO-$D_6$, PPM), 11.18 (1H, s broad), 7.95 (2H, s), 5.20 (1H, dd, J=5.0, 11.3), 2.95–2.80 (1H, m), 2.65–2.4 (2H, m), 2.1–1.95 (1H, m).

Example 10

Synthesis of 3-hydrazine-6-chloro-thalidomide.HCl: Into a hot solution of (3.22 g, 10 mmols) 3,6-dichlorotholidomide in 50 mL of THF anhydrous, 1.2 mL (21 mmols) hydrazine anhydride was added. The reaction mixture was heated at reflux for about 1 hour. After about 30 minutes white solid product started forming. The solid product was separated and washed with 20 mL THF and recystalized from isopropanol. 1H NMR in DMSO-$D_6$ confirmed the product as 3, hydrazine-6-chloro-thalidomide-hydrogen chloride. 1H NMR (DMSO-$D_6$, PPM), 10.85 (1H, s broad), 9.25 (1H, s broad), 8.60 (1H, d, J=9.5), 7.55 (2H, s, aromatic), 4.65 (1H, dd, J=5.0, 11.2), 4.45(2H, s broad), 2.7–2.65 (1H, m), 2.65–2.45 (2H, m), 2.05–1.90 (3H, m).

Example 11

Synthesis of 3,6-dihydrazino-thalidomide.HCl: Into a hot solution of (3.22 g, 10 mmols) 3,6-dichlorotholidomide in 10 mL of DMF anhydrous, 1.2 mL (21 mmols) hydrazine anhydride was added. The reaction mixture was heated at reflux for about 1 hour. The DMF was evaporated and product was crystallized from isopropanol. 1H NMR in DMSO-$D_6$ confirmed the product as 3,6-dihydrazinothalidomide-hydrogen chloride. 1H NMR (DMSO-$D_6$, PPM), 10.85 (1H, s broad), 9.25 (2H, s broad), 8.58 (2H, d, J=9.5), 7.55 (2H, s, aromatic), 4.65 (1H, dd, J=5.0, 11.2), 4.45(4H, s broad), 2.7–2.65 (1H, m), 2.65–2.45 (2H, m), 2.05–1.90 (3H, m).

Example 12

Synthesis of 3,6-diamino-thalidomide: A mixture of (4.08 g, 20 mmols) 3,6-dichlorotholidomide and ammonium acetate (21 mmols) was heated until a melt was formed and then ammonia gas was bubbled (three to four bubbles per minute) in to the mixture for six hours at 160–170° C. The reaction mixture was cooled and broken in to powder. On adding water white solid product started forming. The solid product was separated and washed with 20 mL water and recystalized from MeOH. 1H NMR in DMSO-$D_6$ confirmed the product as 3,6-diamino-tholidomide.

Example 13

Synthesis of methyl-2-bromomethyl-3-nitrobenzoate: Into a stirring solution of methyl-2-methyl-3-nitrobenzoate (3.9 g, 20 mmols) in 50 mL $CCl_4$ anhydrous, N-bromosuccinamide (7.2 g, 40 mmols), and Benzoylperoxide (26 mg, 0.10 mmols), was added. The reaction mixture was heated under reflux for about 18 hours. TLC developed in EtOAc/Hex 1:9 mixture showed formation of new product. The $CCl_4$ layer was filtered and evaporated and on leaving viscos product at RT light yellow crystals of product were separated. The product was purified by flash silica gel column eluted with Hex/EtOAc. 9:1 mixture to give 4.0 g light yellow crystals (90%). 1H NMR in CDCl3 confirmed the product as methyl-2-bromomethyl-3-nitrobenzoate. 1H NMR ($CDCl_3$, PPM), 8.1 (1H, d, J=8.1), 7.95 (1H, d, J=7.1), 7.6 (1H, t, J=8.1), 5.15 (2H, s), 4.05 (3H, s).

Example 14

Synthesis of 3-(4-nitrophthalimidino)-glutarimide: Into a solution of 3-amino-gluteramide-HBr (2.09 g, 10 mmols) in 20 mL of DMF anhydrous, 2.8 mL triethylamine (20 mmols), and methyl-2-bromomethyl-3-nitrobenzoate. (2.78 g, 10 mmols) was added. The reaction mixture was heated at about 90–110° C. for about 2 hours. On cooling the reaction mixture at 0° C., white crystals of product and tri-ethylamine-HBr were formed. After separating crystals the product was crystallized out from hot water, dried under vacume and recrystallized from boiling ethyl alcohol. 1H NMR in DMSO-D6 confirmed the product as 3-(4-nitrophthalimidino)-glutarimide. 1H NMR (DMSO-$D_6$, PPM), 11.05 (1H, s broad), 8.45 (1H, d, J=7.6), 8.20 (1H, d, J=7.5), 8.15 (1H, t, J=8.3), 5.2 (1H, dd, J=5.1, 13.2), 4.9 (2H, dd, J=12.2, 17.5), 3.00–2.85 (1H, m), 2.65–2.4 (2H, m), 2.05–1.90 (1H, m).

Example 15

Synthesis of 3-(4-aminophthalimidino)-glutarimide: A solution of 3-(4-nitrophthalimidino)-glutarimide (1.7 g, 6.3 mmols) was dissolved in 100 mL dioxane/methanol 4:1 mixture and hydrogenated in Parr hydrogenater at about 40 psi of hydrogen in the presence of Pd/C 5% (500 mg) for about 4 hours. After filtering the reaction mixture through Celite filtering agent the solvents were evaporated under vacuum to give white powder. 1H NMR in DMSO-$D_6$ confirmed the product as 3-(4-aminophthalimidino)-glutarimide. 1H NMR (DMSO-$D_6$, PPM), 11.95 (1H, s broad), 8.05 (1H, t, J=8.3), 7.90 (1H, d, J=7.5), 7.85 (1H, d, J=7.3), 6.3 (2H, s), 5.95 (1H, dd, J=5.1, 13.2), 5.0 (2H, dd, J=12.2, 15.2), 3.55–3.45 (1H, m), 3.30–3.25 (1H, m), 3.05–3.0 (1H, m), 2.75–2.65 (1H, m).

Example 16

Synthesis 3-(4-hydrazinophthalimidino)-glutarimide: Into a solution of 3-(4-aminophthalimidino)-glutarimide (256 mg, 1.0 mmols) in 12 mL HCl (conc)/water 2:1 mixture, sodium nitrite (80 mg, 2.2 mmol) in 2 mL water was added at about 0° C. and stirred for about 10 min. After adding Tin(II) chloride (556 mg, 3 mmol) at 0° C., the reaction mixture was stirred for about 1 hour at 0° C. to RT. After about 1 hour, the solvents were evaporated under vacuum to give a yellow powder. The product was recryrstallized from water to afford 200 mg (80%) of 3-(4-hydrazinophthalimidino)-glutarimide. The free base of 3-hydrazino-thalidomide was prepared by dissolving the product in to acetone and then passing it over dry sodium bicarbonate. After evaporating acetone, the product was recrystallized from absolute ethanol. 1H NMR in DMSO-$D_6$ confirmed the product as 3-(4-hydrazinophthalimidino)-glutarimide. 1H NMR (DMSO-$D_6$, PPM), 10.95 (1H, s broad), 8.65 (1H, s broad), 7.3 (1H, t, J=7.2), 7.25 (1H, d, J=8.1), 7.05 (1H, d, J=7.3), 5.15 (1H, dd, J=5.1, 13.2), 4.45 (2H, dd, J=12.2, 15.2), 3.0–2.85 (1H, m), 2.65–2.55 (1H, m), 2.45–2.3 (1H, m), 2.05–1.95 (1H, m), 1.9 (2H, s).

Example 17

Synthesis 3-(6-hydrazinophthalimidino)-glutarimide: This product was synthesized in accordance with Example 16, except that 3-(6-aminophthalimidino)-glutarimide was substituted for 3-(4-aminophthalimidino)-glutarimide.

Example 18

Synthesis 3-(7-hydrazinophthalimidino)-glutarimide: This product was synthesized in accordance with Example 16, except that 3-(7-amino-phthalimidino)-glutarimide was substituted for 3-(4-aminophthalimidino)-glutarimide.

Example 19

Synthesis of methyl-2-methyl-6-nitrobenzoate: A portion of 2-methyl-6-nitrobenzoic acid (9.05 g, 50 mmols) and phosphorous pentachloride (10.4 g, 50 mmols) were mixed together. Soon, HCl gas started coming out and the solids changed into a transparent liquid. The evolution of HCl gas was trapped in a water container, and when no more gas evolved (about 20 min.), the reaction was stopped. Phosphorus oxychloride by-product was distilled under vacuum. On adding 20 mL MeOH, an exothermic reaction occurred and then solvents were evaporated under reduced pressure. The product was purified by flash silica gel column eluted with Hex/CHCl$_3$. 1:1 mixture to give 8.1 g viscous product which solidified on standing (90%). 1H NMR in CDCl$_3$ confirmed the product as methyl-2-methyl-6-nitrobenzoate.

Example 20

Synthesis of methyl-2-bromomethyl-6-nitrobenzoate: Into a stirring solution of methyl-2-methyl-6-nitrobenzoate (3.9 g, 20 mmols) in 50 mL CCl$_4$ anhydrous, N-bromosuccinamide (3.56 g, 20 mmols), and benzoylperoxide (25 mg, 0.10 mmols), was added. The reaction mixture was heated under reflux for about 24 hours. TLC developed in EtOAc/Hex 1:9 mixture showed formation of new product. The CCl$_4$ was evaporated and on leaving a viscous product at RT, light yellow crystals of product were separated. The product was purified by flash silica gel column eluted with Hex/EtOAc. 9:1 mixture to give 3.0 g light yellow crystals (70%). A small portion of dibrominated product was also separated. 1H NMR in CDCl$_3$ confirmed the product as methyl-2-bromomethyl-6-nitrobenzoate.

Example 21

Synthesis of 3-(7-nitrophthalimidino)-glutarimide: Into a solution of 3-amino-gluteramide-HBr (2.09 g, 10 mmols) in 20 mL of DMF anhydrous, 2.8 mL triethylamine (20 mmols) and methyl-2-bromomethyl-6-nitrobenzoate (2.78 g, 10 mmols) was added. The reaction mixture was heated at about 90–110° C. for about 2 hours. On cooling reaction mixture at 0° C. white crystals of product and tri-ethylamine-HBr were formed. After separating crystals of Et3N-HBr product was crystallized out from hot water, dried under vacuum and recrystallized from hot MeOH. 1H NMR in DMSO-D6 confirmed the product as 3-(7-nitrophthalimidino)-glutarimide.

Example 22

Synthesis of 3-(7-aminophthalimidino)-glutarimide: A solution of 3-(7-nitrophthalimidino)-glutarimide (1.7 g, 6.3 mmols) was dissolved in 100 mL dioxane/methanol 4:1 mixture and hydrogenated in Parr hydrogenater at about 40 psi of hydrogen in the presence of Pd/C 5% (500 mg) for about 4 hours. After filtering the reaction mixture through Celite filtering agent the solvents were evaporated under vacuum to give white powder. 1H NMR in DMSO-D6 confirmed the product as 3-(7-aminophthalimidino)-glutarimide.

Example 23

Synthesis of 3-(6-nitrophthalimidino)-glutarimide: Into a solution of 3-phthalimidino-glutarimide (EM-12) (2.45 g, 10 mmols) in 12 mL of sulfuric acid conc., a 12 mL portion of a 1:1 mixture of sulfuric acid conc, and nitric acid conc, was added at about 0° C. The reaction mixture was stirred at about 0° C. for about 1 hour and then the temperature was raised to RT for about 30 min. On pouring reaction mixture in 50 mL ice, the product was crystallized out from water, dried under vacuum and recrystallized from hot MeOH. $^1$H NMR in DMSO-D$_6$ confirmed the product as 3-(6-Nitrophthalimidino)-glutarimide.

Example 24

Synthesis of 3-(6-aminophthalimidino)-glutarimide: A solution of 3-(6-nitrophthalimidino)-glutarimide (1.45 g, 5.0 mmols) was dissolved in 100 mL dioxane/methanol 4:1 mixture and hydrogenated in Parr hydrogenater at about 40 psi of hydrogen in the presence of Pd/C 5% (700 mg) for about 4 hours. After filtering the reaction mixture through Celite filtering agent the solvents were evaporated under vacuum to give white powder. 1H NMR in DMSO-D6 confirmed the product as 3-(6-aminophthalimidino)-glutarimide.

Example 25

Synthesis of 2-(6-nitrophthalimidino)-glutaric acid: Into a solution of 3-phthalimidino-glutaric acid (EM-138) (2.63 g, 10 mmols) in 12 mL of sulfuric acid conc., a 12 mL portion of a 1:1 mixture of sulfuric acid conc. and nitric acid conc. was added at about 0° C. The reaction mixture was stirred at about 0° C. for about 1 hour and then the temperature was raised to RT for about 30 min. On pouring reaction mixture in 50 mL ice, the product was crystallized out from water, dried under vacuum to give 2.5 g (80%) white solid. $^1$H NMR in DMSO-D$_6$ confirmed the product as 2-(6-nitrophthalimidino)-glutaric acid.

Example 26

Synthesis of 3-(6-aminophthalimidino)-glutaric acid: A solution of 3-(6-nitrophthalimidino)-glutaric acid (1.6 g, 5.0 mmols) was dissolved in 100 mL dioxane/methanol 4:1 mixture and hydrogenated in Parr hydrogenater at about 40 psi of hydrogen in the presence of Pd/C 5% (700 mg) for about 4 hours. After filtering the reaction mixture through Celite filtering agent the solvents were evaporated under vacuum to give white foamy solid. 1H NMR in DMSO-D6 confirmed the product as 3-(6-aminophthalimidino)-glutaric acid. 1H NMR (DMSO-D$_6$, PPM), 7.30 (1H, d, J=8.1), 6.75 (1H, s,), 6.60 (1H, d, J=7.1), 4.75 (1H, dd, J=4.1, 7.7), 4.32 (2H, s), 2.35–2.20 (3H, m), 2.10–1.95 (1H, m).

Example 27

Synthesis of 3-(7-Nitrophthalimidino)-glutaric acid diethylester: Into a solution of L-glutamic acid diethylester hydrochloride (2.7 g, 11 mmols) in 10 mL of DMF anhydrous, 3.5 mL triethylamine (25 mmols), and methyl-2-bromomethyl-6-nitrobenzoate (2.78 g, 10 mmols) was added. The reaction mixture was heated at about 70–80° C. for about 2 hours. After adding 30 mL 1N HCl, the product was extracted with ethyl acetate. The ethyl acetate layer was washed with water, dried over brine and Na$_2$SO$_4$ anhydrous, filtered, and evaporated to give viscous product. The product was purified by flash silica gel column eluted with Hex/EtOAc. 1:1 mixture to give 3.5 g purified product (70%). 1H NMR in CDCl3 confirmed the product as 3-(7-Nitrophthalimidino)-glutaric acid diethylester.

Example 28

Synthesis of 3-(7-aminophthalimidino)-glutaric acid diethylester: A solution of 3-(7-nitrophthalimidino)-glutaric acid diethylester (1.2 g, 5.0 mmols) was dissolved in 100 mL methanol and hydrogenated in Parr hydrogenater at about 40 psi of hydrogen in the presence of Pd/C 5% (500 mg) for about 4 hours. After filtering the reaction mixture through Celite filtering agent, the solvents were evaporated under vacuum to give viscous product. 1H NMR in $CDCl_3$ confirmed the product as 3-(7-aminophthalimidino)-glutaric acid diethylester.

Example 29

Synthesis of 3-(7-aminophthalimidino)-glutaric acid: A solution of 3-(7-nitrophthalimidino)-glutaric acid diethylester (1.65 g, 5.0 mmols) in 2 mL conc. HCl was mixed with 2 mL of acetic acid and then reaction mixture was heated under reflux for about 1 hour. After evaporating acids under vacuum, the foamy solid was washed with ether and dried under vacuum. The product was crystallized out from isopropanol/ether mixture, and dried under vacuum to give 1.1 g (80%) white solid. 1H NMR in DMSO-$D_6$ confirmed the product as 3-(7-aminophthalimidino)-glutaric acid hydrochlorider. 1H NMR (DMSO-$D_6$, PPM), 7.30 (1H, t, J=8.1), 6.75 (1H, d, J=7.5), 6.60 (1H, d, J=7.1), 4.75 (1H, dd, J=4.1, 7.7), 4.32 (2H, s), 2.35–2.20 (3H, m), 2.10–1.95 (1H, m).

Example 30

Synthesis of 3-(4-Nitrophthalimidino)-glutaric acid diethylester: Into a solution of L-glutamic acid diethylester hydrochloride (2.7 g, 11 mmols) in 10 mL of DMF anhydrous, 3.5 mL triethylamine (25 mmols) and methyl-2-bromomethyl-3-nitrobenzoate (2.78 g, 10 mmols) were added. The reaction mixture was heated at about 70–80° C. for about 2 hours. After adding 30 mL 1N HCl, the product was extracted with ethyl acetate. The ethyl acetate layer was washed with water, dried over brine and $Na_2SO_4$ anhydrous, filtered, and evaporated to give viscous product. The product was purified by flash silica gel column eluted with Hex/EtOAc. 1:1 mixture to give 3.5 g purified product (70%). 1H NMR in CDCl3 confirmed the product as 3-(7-Nitrophthalimidino)-glutaric acid diethylester.

Example 31

Synthesis of 3-(4-aminophthalimidino)-glutaric acid diethylester: A portion of 3-(4-nitrophthalimidino)-glutaric acid diethylester (1.2 g, 5.0 mmols) was dissolved in 100 mL methanol and hydrogenated in a Parr hydrogenater at about 40 psi of hydrogen in the presence of Pd/C 5% (500 mg) for about 4 hours. After filtering the reaction mixture through Celite filtering agent the solvents were evaporated under vacuum to give viscous product. 1H NMR in $CDCl_3$ confirmed the product as 3-(7-aminophthalimidino)-glutaric acid diethylester.

Example 32

Synthesis of 3-(4-aminophthalimidino)-glutaric acid: A solution of 3-(4-nitrophthalimidino)-glutaric acid diethylester (1.65 g, 5.0 mmols) in 2 mL conc. HCl was mixed with 2 mL of acetic acid and then reaction mixture was heated under reflux for about 1 hour. After evaporating acids under vacuum, the foamy solid was washed with ether and dried under vacuum. The product was crystallized out from isopropanol/ether mixture, and dried under vacuum to give 1.1 g (80%) white solid. 1H NMR in DMSO-$D_6$ confirmed the product as 3-(7-aminophthalimidino)-glutaric acid hydrochlorider. 1H NMR (DMSO-$D_6$, PPM), 7.45 (1H, t, J=8.1), 7.35 (1H, d, J=7.5), 7.30 (1H, d, J=7.1), 4.85 (1H, dd, J=5.1, 12.2), 4.45 (2H, s), 2.35–2.20 (3H, m), 2.10–1.95 (1H, m), 1.75 (2H, s).

Example 33

Synthesis of 3-(4-dimethylamino-phthalimidino)-glutaric acid diethylester: Into a solution of 3-(4-aminophthalimidino)-glutaric acid diethylester (278 mg, 0.8 mmols) in 2 mL DMF anhydrous, 300 mg (2 mmol) of $K_2CO_3$, 0.25 mL iodomethane (4 mmol), and 0.45 mL triethylamine was added. The reaction mixture was heated to about 60–70° C. for about 2 hours. The reaction mixture was diluted with 10 mL water and product was extracted with ethyl acetate. The ethyl acetate layer was washed with water, dried over brine and $Na_2SO_4$ anhydrous, filtered, and evaporated to give viscous product. The product was purified by flash silica gel column eluted with Hex/EtOAc. 1:1 mixture to give 235 mg purified product (70%). 1H NMR in $CDCl_3$ confirmed the product as 3-(4-dimethylamino-phthalimidino)-glutaric acid diethylester.

Example 34

Synthesis of 3-(4-aminophthalimidino)-glutaric acid: A solution of 3-(4-dimethylamino-phthalimidino)-glutaric acid diethylester (180 mg, 0.5 mmols) in 2 mL conc. HCl was mixed with 2 mL of acetic acid and then reaction mixture was heated under reflux for about 1 hour. After evaporating acids under vacuum, the foamy solid was washed with ether and dried under vacuum. The product was crystallized out from isopropanol/ether mixture, and dried under vacuum to give 131 mg (80%) white solid. 1H NMR in DMSO-$D_6$ confirmed the product as 3-(4-dimethylamino-phthalimidino)-glutaric acid hydrogen chloride.

Example 35

Synthesis of 3-(2-nitrobenzamido)-glutarimide: Into a solution of 3-amino-gluteramide-HBr (2.09 g, 10 mmols) in 20 mL of DMF anhydrous, 2.8 mL triethylamine (20 mmols) and 2-nitrobenzoyl chloride (1.78 g, 10 mmols) was added at about 0° C. The reaction mixture was stirred at RT for about 2 hours. On cooling reaction mixture at $_0$° C., white crystals of product and tri-ethylamine-HBr were formed. After separating crystals the product was crystallized out from hot water, dried under vacuum and recrystallized from boiling ethyl alcohol. 1H NMR in DMSO-D6 confirmed the product as 3-(2-nitrobenzamino)-glutarimide.

Example 36

Synthesis of 3-(2-aminobenzamido)-glutarimide: This product was produced in accordance with Example 31, except that 3-(2-nitrobenzamino)-glutarimide replaced 3-(4-nitrophthalimidino)-glutaric acid diethylester. 1H NMR in DMSO-$D_6$ confirmed the product as 3-(2-aminobenzamido)-glutarimide.

Example 37

Preparation of 3,6-diaminophthalic acid: To a solution of 3,6-dinitrophthalic acid[1] (1.0 g, 3.90 mmol) in 20% methanol in dioxane (40 mL) was added 5% Palladium on activated carbon, and hydrogenated in Parr Hydrogenator at 60 psi of hydrogen for 3 h. The reaction mixture was filtered through a pad of celite and concentrated in vacuo. A green powder was obtained (0.60 g, 78%). $^1$H NMR (300 MHz, DMSO) δ 7.69 (br s, 5.3H, ArNH$_2$), 6.70 (s, 2.0H, ArH).

Example 38

Preparation of 3,6-di-N-Boc-diaminophthalic acid: To 3,6-diaminophthalic acid (0.443 g, 2.26 mmol) in methanol (23 mL) was added triethylamine (1.4 mL, 9.49 mmol) followed by the di-tert-butyl dicarbonate (1.04 mL, 4.52 mmol) and heated to reflux for about 4 hours. Methanol was removed in vacuo and the reaction mixture dissolved in 1 M HCl (10 mL), extracted with ethyl acetate (2×20 mL), this combined organic pool washed with water (1×10 mL), brine (1×10 mL), dried (Na$_2$SO$_4$), filtered and concentrated in vacuo. A yellow-green powder was obtained (0.468 g, 52%). $^1$H NMR (300 MHz, DMSO) δ 8.83 (m, 2.1H, ArH), 8.15 (s, 1.1H, ArNH), 7.78 (s, 1.0H, ArNH), 1.50 (br s, 9.9H, —OC(CH$_3$)$_3$), 1.44 (br s, 9.6H, —OC(CH$_3$)$_3$).

Example 39

Preparation of 3,6-di-N-Boc-aminophthalic anhydride: 3,6-di-N-Boc-diaminophthalic acid (0.468 g, 1.18 mmol) in acetic anhydride (12 mL) was heated to about 100° C. for about 0.5 hour. The solvent was removed and the product dried in vacuo overnight. A yellow solid was obtained (0.446 g, 100%). $^1$H NMR (300 MHz, DMSO) δ 8.82 (s, 2.1H, ArH), 8.18 (s, 2.0H, ArNH), 1.50 (br s, 21.8H, —OC(CH$_3$)$_3$).

Example 40

Preparation of 3,6-di-N-Boc-amino-thalidomide: 3,6-di-N-Boc-aminophthalic anhydride (0.470 g, 1.24 mmol) and 3-amino-glutarimide-HBr (0.259 g, 1.24 mmol) in pyridine (5 mL) were heated to about 100° C. for about 3 hours. The pyridine was removed in vacuo, and the residue was diluted with 1M HCl (3 mL). The brown solid was filtered and dried. This crude mixture was purified by flash chromatography using the Biotage 40M Column (5% methanol in chloroform). A yellow precipitate was obtained (0.256 g, 42%). $^1$H NMR (300 MHz, DMSO) δ 11.2 (s, 1.0H, NH), 8.73 (s, 2.1H, OCONHAr), 8.20 (s, 2.1H, ArH), 5.10 (dd, 1.4H, J=12.8, 5.4 Hz, NCHCO), 2.87 (m, 1.6H, —CH$_2$—), 2.60 (m, 2.2H, —CH$_2$—), 2.04 (m, 1.6H, —CH$_2$—), 1.48 (br s, 21.9H, —OC(CH$_3$)$_3$).

Example 41

Preparation of 3,6-di-amino-thalidomide: To 3,6-di-N-Boc-amino-thalidomide (0.107 g, 0.219 mmol) in CH$_2$Cl$_2$ (2.1 mL) was added trifluoroacetic acid (0.90 mL) and stirred for about 2 hours. The solvent was removed, and the residue triturated with diethyl ether. An orange solid was obtained and dried in vacuo overnight (0.060 g, 95%). $^1$H NMR (300 MHz, DMSO) δ 11.1 (s, 1.0H, NH), 6.90 (s, 2.0H, ArH), 6.17 (br s, 5.9H, ArNH$_3^+$), 4.97 (dd, 1.0H, J=12.5, 5.4, NCHCO), 2.85 (m, 1.1H, —CH$_2$—), 2.57 (m, 1.5H, —CH$_2$—), 1.97 (m, 1.1H, —CH$_2$—). Anal. Calcd. for C$_{13}$H$_{12}$N$_4$O$_4$.1TFA: C, 44.78; H, 3.26; F, 14.17; N, 13.93; O, 23.86. Found: C, 44.24; H, 3.57; N, 13.24; O, 25.55.

Example 42

Preparation of 3,6-di-acetoamidophthalic anhydride: 3,6-diaminophthalic acid (0.21 g, 1.07 mmol) was dissolved in acetic anhydride (10 mL) at about 100° C., and stirred at this temperature for about 0.5 hour. After the reaction was cooled the product was filtered and washed with ether. A yellow precipitate was obtained (0.243 g, 86%). $^1$H NMR (300 MHz, DMSO) δ 9.85 (s, 2.0H, CONHAr), 8.29 (s, 2.1H, ArH), 2.17 (br s, 6.2H, COCH$_3$).

Example 43

Preparation of 3,6-di-acetoamido-thalidomide: To 3,6-di-acetoamidophthalic anhydride (0.100 g, 0.38 mmol) and 3-amino-glutarimide-HBr (0.079 g, 0.38 mmol) in pyridine (2 mL) was heated to about 100° C. for about 18 hours. The reaction was concentrated in vacuo, triturated with 1 M HCl (3 mL), the precipitated product was then filtered and washed with water. A yellow powder was obtained (0.080 g, 57%). $^1$H NMR (300 MHz, DMSO) δ 11.1 (s, 1.0H, CONHCO), 9.67 (s, 2.1H, CONHAr), 8.26 (s, 2.1H, ArH), 5.12 (dd, J=12.8, 5.4, 1.1H, NCHCO), 2.92 (m, 1.1H, —CH$_2$—), 2.58 (m, 1.7H, —CH$_2$—), 2.16 (br s, 6.2H, CH$_3$CONH), 2.07 (m, 1.5H, —CH$_2$—).

Example 44

Preparation of 3,6-dichloro-thalidomide: To 3,6-dichlorophthalic anhydride (0.217 g, 1.0 mmol) in pyridine (2 mL) was added 3-amino-glutarimide-HBr (0.209 g, 1.0 mmol) and heated to reflux for about 2 hours. The reaction was diluted with excess H$_2$O (12 mL), the precipitate was filtered, washed with methanol, and dried in vacuo overnight. A colorless solid was obtained (0.198 g, 62%). $^1$H NMR (300 MHz, DMSO) δ 11.2 (s, 1.0H, CONHCO), 7.91 (s, 2.0H, ArH), 5.17 (dd, J=12.7, 5.4, 1.1H, NCHCO), 2.87 (m, 1.1H, —CH$_2$—), 2.59 (m, 1.3H, —CH$_2$—), 2.04 (m, 1.1H, —CH$_2$—).

Example 45

Preparation of 3-hydrazino-6-chloro-thalidomide-HCl: To 3,6-dichloro-thalidomide (0.491 g, 1.5 mmol) in THF (15 mL) was added anhydrous hydrazine (96 mg, 3.0 mmol), and heated to reflux for about 0.5 hour. The precipitated product was filtered from the cooled reaction mixture and washed with fresh THF. This crude product was recrystalized from IPA to give 3-hydrazino-6-chloro-thalidomide-HCl as a white crystalline solid (0.310 g, 65%). $^1$H NMR (300 MHz, DMSO) δ 10.9 (s, 1.1H, CONHCO), 9.27 (s, 1.0H, ArNH), 8.64 (d, J=8 Hz, 1.1H, ArNH), 7.60 (s, 3.1H, ArH), 4.66 (m, 1.6H, NCHCO), 4.42 (br s, 2.2H, NHNH$_2$), 2.70 (m, 1.7H, —CH$_2$—), 2.55 (m, 1.0H, —CH$_2$—), 1.98 (m, 3.3H, —CH$_2$—). $^{13}$C NMR (300 MHz, DMSO) δ 173.8, 172.1, 164.2, 163.8, 137.1, 136.3, 132.0, 131.9, 130.3, 129.8, 50.3, 31.4, 24.8. Anal. Calcd. for C$_{13}$H$_{11}$ClN$_4$O$_4$.1HCl: C, 43.47; H, 3.37; Cl, 19.74; N, 15.60; O, 17.82. Found: C, 43.74; H, 3.51; Cl, 19.47; N, 15.41; O, 18.02.

The free diacid was obtained using the procedure from J. Chromatography, 266, 1983, 401–408, which is incorporated herein by reference. The 3,6-dinitrophthalic acid, pyridine salt (2.0 g) from Sigma (D-2880) was suspended in 6M HCl (2 mL) and extracted with ether (2×20 mL). The combined organic pool was washed with water (1×5 mL), dried (Na$_2$SO$_4$), filtered and concentrated in vacuo.

Example 46

Synthesis of S-(-)-(3-benzyloxycarbonylamino)-glutarimide: Into a stirring solution of carboxybenzyloxy-L-glutamine (2.8 g, 10 mmols) in 40 mL dichloromethane anhydrous, N,N-Dicyclohexylcabdiimide (DCC) (1.92 g, 12 mmols) and hydoxybenzotriazole (12 mmols) (HOBT) were added. The reaction mixture was stirred for about 18 hours. The reaction mixture was filtered to remove urea bi-product and dichloromethane layer was washed with water and brine and dried over CaSO$_4$ anhydrous, filtered, and evaporated to give white solid. The solid product was crystallized from ethyl ether to give 2.4 grams crystalline powder (90%). $^1$H NMR in CDCl$_3$ confirmed the product as S-(-)-(3-benzyloxycarbonylamino)-glutarimide.). 1H NMR (CDCL$_3$, PPM), 8.2 (1H, s broad), 7.4 (5H, s, aromatic), 5.8 (1H, d), 5.15 (2H, s), 4.4 (1H, dd, J=4.5, 3), 2.95–2.4 (3H, m), 1.86 (1H, d, t, J=11.5, 6.5). m. p. 122–124° C. (lit=122–124° C.).

Example 47

The Roche Cell Proliferation Kit II (XTT) is an useful assay for screening the relative efficacy of small molecules. The assay quantitatively determines cellular proliferation in response to agonists and/or antagonists of proliferation. It is based on the cleavage of the yellow tetrazolium salt (XTT) by metabolically active/viable cells to form an orange formazan dye. The formation of the soluble dye allows direct quantification using a scanning mulitwell spectrophotometer. An increase in the number of living cells (resulting from proliferation) results in a greater production of formazan dye which corresponds to an increase in the absorbance value.

When evaluating analogs of thalidomide, or the like, we have employed HS-Sultan cells in an in vitro XTT assay. In each well of a 96-well microtiter plate, cells are seeded at a density of 15,000 cells per 90 uL of normal growth media approximately 16 hours prior to treatments. During culture and treatments, cells are maintained at 37° C. with 5% CO$_2$ in a high humidity incubator. Treatments (10×) are added in 10 uL aliquots to achieve a 10× final treatment concentration in each well. Each concentration is done in triplicate. The XTT labeling mixture is added in 50 uL aliquots to each well during the final four hours of the 72 hour treatment period. When the treatment/labeling period is complete, the plate is read on a spectrophotometric plate reader at a wavelength of 470 nm and a 650 nm reference wavelength. For individual experiments, the average absorbance values (with background subtracted) for each treatment are plotted against the uM concentration. A larger absorbance value corresponds to a greater amount of proliferation. A negative control (untreated cells) is used as a point of reference; an absorbance value less than the control reflects an inhibition of proliferation.

Figure 12:
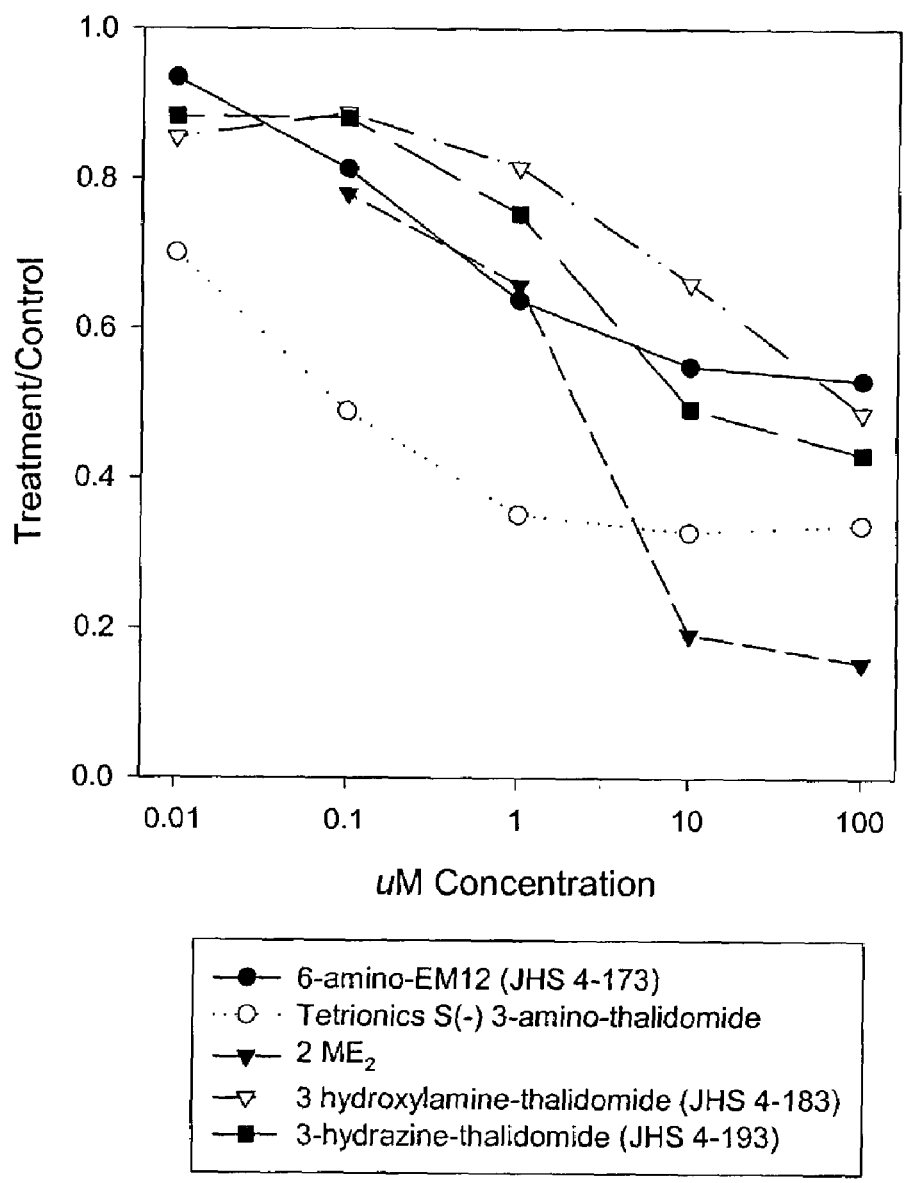
FIGS. 12 through 14 are graphs of respective XTT proliferation assays.
Figure 13:
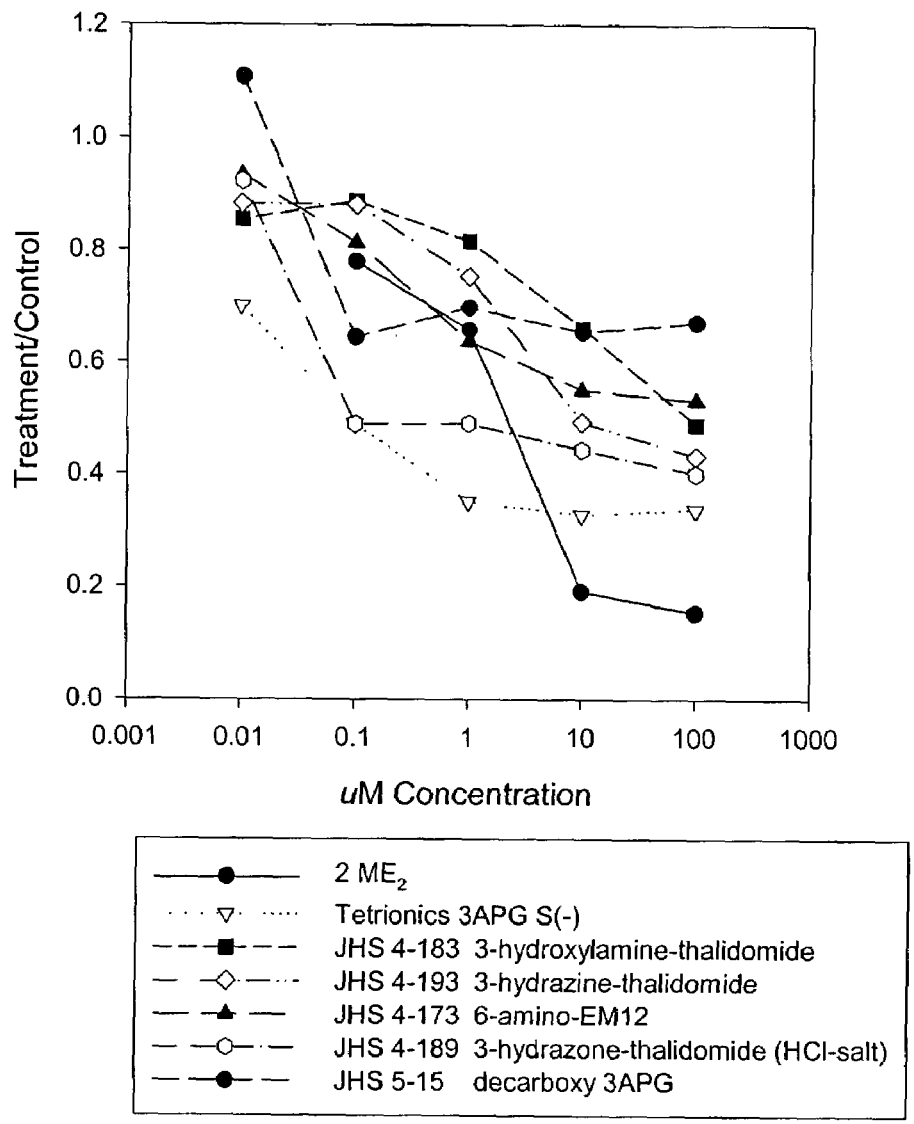
Figure 14:
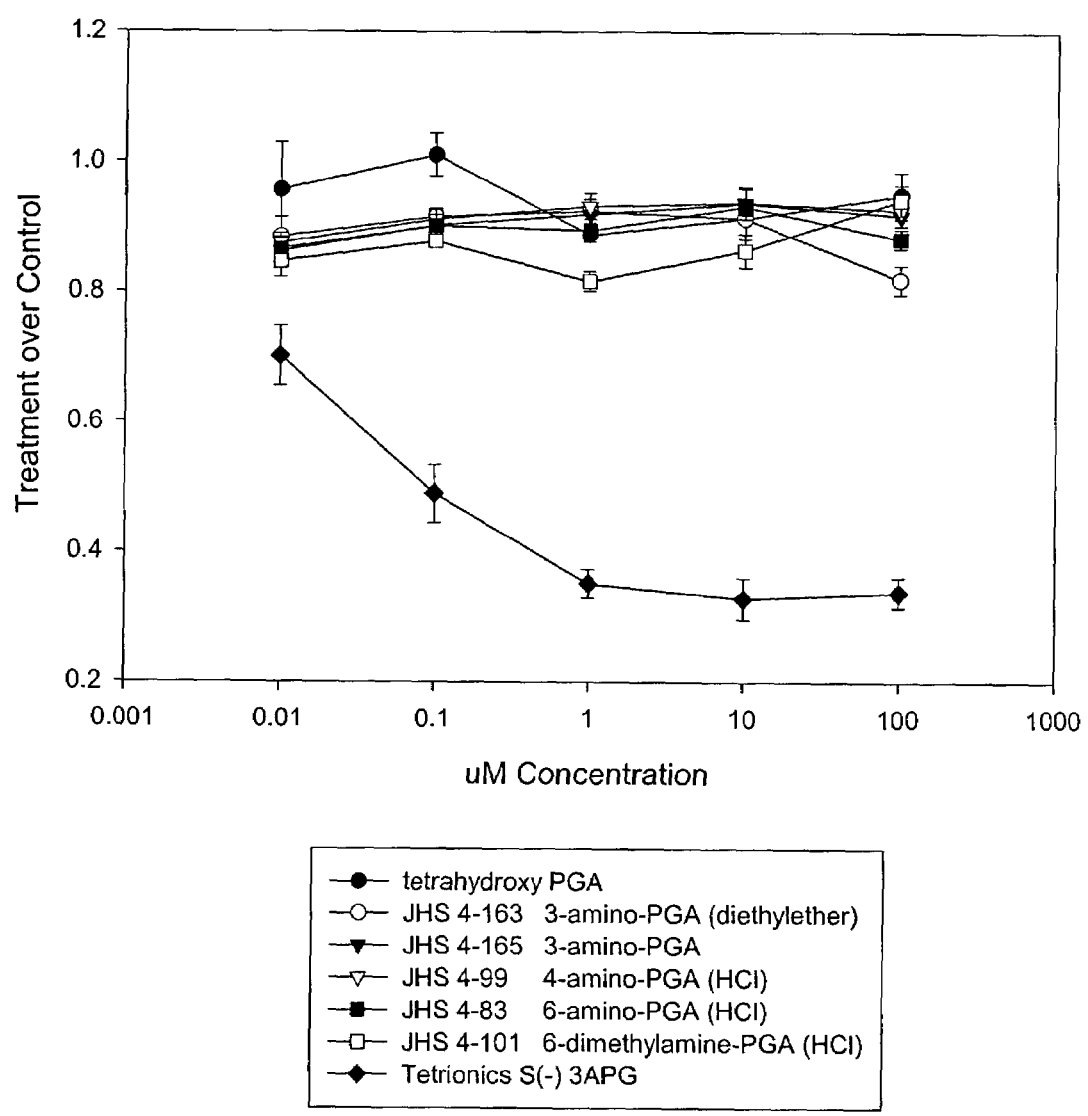

When comparing experiments conducted over a period of time, absorbance values from each experiment may vary due to a number of factors (degradation of the XTT reagents over time is the most common factor). When using reagents from an older XTT kit or switching to a new kit, the overall absorbance values for that individual experiment may be higher or lower, making a direct comparison to another experiment difficult. Therefore, it is often convenient to convert the absorbance values to a ratio of the treated values divided by the negative control value (treatment over control) when comparing the results from multiple experiments; the "treatment over control" values for each treatment are then plotted against the uM concentration. FIGS. 12, 13, and 14 illustrates the results for various compounds in accordance with the present invention.

It should be understood, of course, that the foregoing relates only to preferred embodiments of the present invention and that numerous modifications or alterations may be made therein without departing from the spirit and scope of the invention as set forth in the appended claims.

The invention claimed is:

1. A method of treating macular degeneration in a human or an animal comprising administering to the human or the animal in need thereof a composition comprising an effective amount of a compound of the formula:

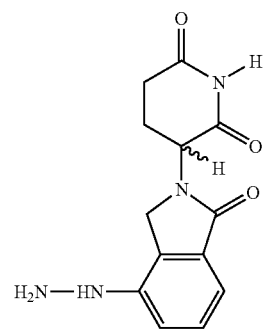

6-Hydrazino-EM-12 to treat macular degeneration.

2. The method of claim 1, wherein the compound is delivered in a pharmaceutically acceptable carrier.

* * * * *